United States Patent
Ahn et al.

(10) Patent No.: US 11,446,402 B2
(45) Date of Patent: *Sep. 20, 2022

(54) COMPOSITION FOR MATERIAL DELIVERY, INCLUDING EXOSOME MIMETICS DERIVED FROM RED BLOOD CELLS, AND USE THEREOF

(71) Applicant: Kyungpook National University Industry—Academic Cooperation Foundation, Daegu (KR)

(72) Inventors: Byeong Cheol Ahn, Daegu (KR); Seung Hyun Son, Daegu (KR); Prakash Gangadaran, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/670,044

(22) Filed: Oct. 31, 2019

(65) Prior Publication Data
US 2020/0138987 A1 May 7, 2020

(30) Foreign Application Priority Data
Nov. 1, 2018 (KR) .................. 10-2018-0133168

(51) Int. Cl.
*A61K 51/12* (2006.01)
(52) U.S. Cl.
CPC ................. *A61K 51/1234* (2013.01)
(58) Field of Classification Search
CPC ............ A61K 51/1203; A61K 51/1234; A61K 49/0097; A61K 49/0032
See application file for complete search history.

(56) References Cited

U.S. PATENT DOCUMENTS

2009/0274630 A1* 11/2009 Huang ............... A61K 47/6901 424/9.321
2017/0143856 A1* 5/2017 Lee .................... A61K 51/1217

FOREIGN PATENT DOCUMENTS

KR 101842768 3/2018

OTHER PUBLICATIONS

Chemical Properties of Technetium, https://web.archive.org/web/20170528151542/http://www.people.vcu.edu/~mhcrosthwait/clrs461/Chemistry_of_Tcupdate.htm, May 28, 2017. (Year: 2017).*
Jang et al., ACS Nano, 2013, 7(9), p. 7698-7710. (Year: 2013).*
Harisa et al., Saudi Pharm. Journal, 2017, 25 p. 8-17. (Year: 2017).*
Matsumoto et al., Acta Neuropathologica Communications, 2017, 5, 71. (Year: 2017).*
2018 World Molecular Imagine Congress (WMIC), Sep. 11-15, 2018 (https://www.xcdsystem.com/wmis/program/ro23cRI/index.cfm?pgid=297%EF%BC%86sid=5223).
Alam et al. "Endogenous inspired biomineral-installed hyaluronan nanoparticles as pH-responsive carrier of methotrexate for rheumatoid arthritis" Journal of Controlled Release, 252:62-72 (2017).
Gangadaran et al. "A new bioluminescent reporter system to study the biodistribution of systematically injected tumor-derived bioluminescent extracellular vesicles in mice" Oncotarget, 8(66):109894-109914 (2017).
Gangadaran et al. "In vivo Non-invasive Imaging of Radio-Labeled Exosome-Mimetics Derived From Red Blood Cells in Mice" Frontiers in Pharmacology, 9 (2018) 13 pp.
Gangadaran et al. "Extracellular vesicles from mesenchymal stem cells activates VEGF receptors and accelerates recovery of hindlimb ischemia" Journal of Controlled Release, 264:112-126 (2017).
Varga et al. "Radiolabeling of Extracellular Vesicles with 99mTc for Quantitative In Vivo Imaging Studies" Cancer Biotherapy & Radiopharmaceuticals, 31(5):168-173 (2016).
Danesh et al. "Exosomes from red blood cell units bind to monocytes and induce proinflammatory cytokines, boosting T-cell responses in vitro" Blood, 123(5):687-696 (2014).
Hwang et al. "Noninvasive imaging of radiolabeled exosome-mimetic nanovesicle using 99mTc-HMPAO" Scientific Reports, 5:15636 (2015) 10 pp.

* cited by examiner

*Primary Examiner* — Michael G. Hartley
*Assistant Examiner* — Leah H Schlientz
(74) *Attorney, Agent, or Firm* — Myers Bigel, P.A.

(57) ABSTRACT

The present invention relates to a composition for material delivery, including exosome mimetics derived from red blood cells, and a use thereof and the composition for material delivery according to an exemplary embodiment of the present invention includes exosome mimetics derived from red blood cells, which are capable of being loaded with a drug, a radioactive material, or a fluorescent material, and thus may be usefully utilized for a drug delivery use, a cell labeling use, a contrast medium, or the like, and when the composition for material delivery according to an exemplary embodiment of the present invention is used, treatment and diagnosis may be simultaneously performed.

15 Claims, 32 Drawing Sheets

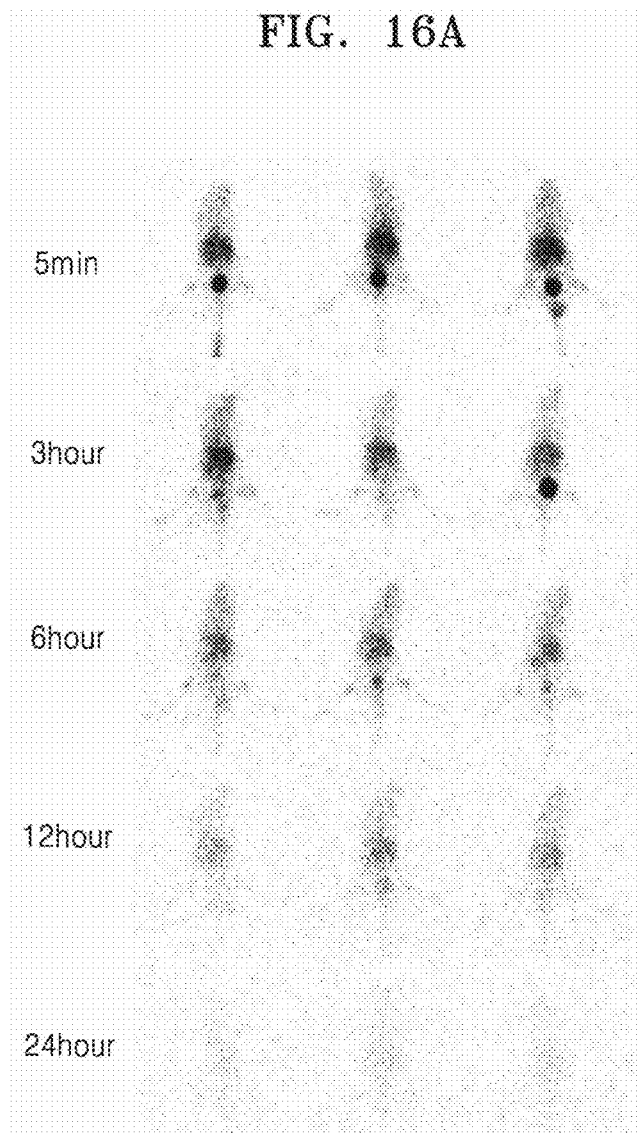

COMPOSITION FOR MATERIAL DELIVERY, INCLUDING EXOSOME MIMETICS DERIVED FROM RED BLOOD CELLS, AND USE THEREOF

CROSS-REFERENCE TO RELATED APPLICATION

This U.S. non-provisional patent application claims priority under 35 U.S.C. § 119 to Korean Patent Application No. 10-2018-0133168, filed on Nov. 1, 2018, in the Korean Intellectual Property Office, the disclosure of which is incorporated herein in its entirety by reference.

TECHNICAL FIELD

The present invention relates to a composition for material delivery, including exosome mimetics derived from red blood cells, and a use thereof, and more particularly, the composition for material delivery according to an exemplary embodiment of the present invention includes exosome mimetics derived from red blood cells, which may be loaded with one or more materials selected from the group consisting of a drug, a radioactive material, and a fluorescent material.

BACKGROUND ART

An exosome is a small vesicle (approximately 30 nm to 100 nm in diameter) with a membrane structure secreted from various cells, is originated from specific intracellular compartments called multivesicular bodies (MVBs), is released and secreted out of cells due to the occurrence of fusion of multivesicular bodies and the plasma membrane, and includes the organization of lipids, proteins, mRNAs, miRNAs, and DNAs abundantly. These exosomes may target a specific tissue, may penetrate into the cell membrane due to the small size, and thus studies using exosomes as a drug carrier to use exosomes for the treatment of various diseases have been recently conducted, but there is a disadvantage in that a lot of time and cost is required to mass-produce and purify exosomes. However, exosome mimetics (EM) can be mass-produced more easily than exosomes while having the advantages of exosomes as they are, and thus have drawn attention as a new drug carrier.

In order to achieve a desired therapeutic effect and control a disease without any side effects, it is important to use a safe drug delivery system which target a specific tissue of the body. Since exosomes produced from various cells may have a completely different distribution in viva, visualization and tracking of exosomes in vivo is important for the development of exosomes as a drug carrier for a specific organ or disease.

Meanwhile, as the average life expectancy of the human is prolonged and interests in a healthy life have been increased, the theranosis (therapy+diagnosis) as a new-concept therapeutic technology which performs both diagnosis and treatment as one of the core medical technologies capable of improving the life quality of patients and patients' families has drawn attention. The theranosis technology which enables diagnosis and treatment of a disease provides an opportunity to ensure a high-quality disease treatment such as selection of a therapeutic agent and determination of the end point of administration of the therapeutic agent by tracking the therapeutic effects of the disease in real time. In order for the technology to be put into practical use within a short period of time, there is a need for a convergence study in various fields, such as development of a biocompatible nanomaterial, securing of a more efficient and safer target-oriented technology, study on an efficient drug delivery system, and development of highly-sensitive diagnostic imaging equipment.

Thus, the inventors of the present application confirmed that when exosome mimetics derived from red blood cells capable of being loaded with various materials were prepared and used, the exosome mimetics could be used as a drug carrier and simultaneously cells could be easily utilized for the labeling use and for the imaging use, thereby completing the present invention.

PRIOR ART DOCUMENT

[Patent Document]
  Korean Patent No. 10-1842768

SUMMARY OF THE INVENTION

The present invention has been made in an effort to provide a composition for material delivery, including exosome mimetics derived from red blood cells, which are loaded with a target material, and a preparation method thereof.

The present invention has also been made in an effort to provide a contrast medium including the composition for material delivery.

An exemplary embodiment of the present invention provides a composition for material delivery, including exosome mimetics derived from red blood cells, which are loaded with a target material.

In the present invention, "exosome mimetics derived from red blood cells" are vesicles artificially prepared by extruding red blood cells by a filter, and are differentiated from exosomes naturally secreted out of cells due to the occurrence of fusion of multivesicular bodies and the plasma membrane. According to an exemplary embodiment of the present invention, "exosome mimetics derived from red blood cells" can be mass-produced while having size and morphological characteristics similar to those of naturally secreted exosomes.

In the present invention "loading" means, for example, that a target material is included inside exosome mimetics derived from red blood cells, or is bound to a membrane of the exosome mimetics derived from red blood cells, but is not limited as long as the target material may be in a form capable of being moved along with the exosome mimetics derived from red blood cells.

The composition for material delivery according to an exemplary embodiment of the present invention can be mass-produced, easily penetrates into tissues due to the small size thereof, and may be utilized as a composition for material delivery by including exosome mimetics derived from red blood cells, which are likely to be degraded by an immune system and have low cytotoxicity.

According to an exemplary embodiment of the present invention, the exosome mimetics derived from red blood cells may have a diameter of 30 nm to 400 nm. More specifically, the exosome mimetics derived from red blood cells may have a diameter of 40 nm to 380 nm, 50 nm to 370 nm, 55 nm to 360 nm, 60 nm to 350 nm, 65 nm to 340 nm, 70 nm to 330 nm, 75 nm to 320 nm, 80 nm to 310 nm, 90 nm to 300 nm, or 95 nm to 300 nm. Preferably, the exosome mimetics derived from red blood cells may have a diameter of 100 nm to 300 nm.

In the present invention, "target material" means a material which may be loaded onto exosome mimetics derived from red blood cells to be moved to a desired place or remain in the desired place, and according to an exemplary embodiment of the present invention, the target material may be one or more selected from the group consisting of a drug, a radioactive material, and a fluorescent material.

In the present invention, "drug" means a material which may be loaded onto the exosome mimetics derived from red blood cells to be delivered to cells or tissues, and thus has a therapeutic effect against a disease. According to an exemplary embodiment of the present invention, the drug may be one or more selected from the group consisting of a compound, a peptide, a protein, and a nucleic acid, which exhibit a preventive or therapeutic effect against a disease.

According to an exemplary embodiment of the present invention, the nucleic acid may be one or more selected from the group consisting of an RNA, a DNA, a short interfering RNA (siRNA), an aptamer, an antisense oligodeoxynucleotide (ODN), an antisense RNA, a ribozyme, a DNAzyme, and a microRNA.

According to an exemplary embodiment of the present invention, the radioactive material may be a diagnostic radionuclide or a therapeutic radionuclide.

According to an exemplary embodiment of the present invention, the diagnostic radionuclide is used to diagnose a disease, and may be one or more selected from the group consisting of $^{99m}$Tc, $^{131}$I, $^{123}$I, and $^{111}$In, but preferably, the diagnostic radionuclide may be technetium-99m ($^{99m}$Tc).

According to an exemplary embodiment of the present invention, the technetium-99m ($^{99m}$Tc) may be bound to hemoglobin inside exosome mimetics derived from red blood cells.

According to an exemplary embodiment of the present invention, the therapeutic radionuclide can be any one as long as the therapeutic radionuclide may be used for the treatment of a human body, including a beta ray-emitting radionuclide. A radiation-emitting nuclide may include a gamma ray-emitting nuclide, and a nuclide which simultaneously emits beta rays and gamma rays, in addition to a pure beta ray-emitting nuclide. According to an exemplary embodiment of the present invention, the therapeutic radionuclide may be one or more selected from the group consisting of $^{131}$I, $^{186}$Re, $^{188}$Re, $^{153}$Sm, and $^{32}$P.

According to an exemplary embodiment of the present invention, the fluorescent material may be one or more selected from the group consisting of a fluorescent protein, a photoprotein, a luciferase, and a fluorescent dye.

According to an exemplary embodiment of the present invention, the fluorescent material may be porphyrin or 1,1'-dioctadecyl-3,3,3',3'-tetramethylindodicarbocyanine perchlorate (DiD).

According to an exemplary embodiment of the present invention, the composition for material delivery may be used to treat a liver disease.

Since a composition for material delivery according to an exemplary embodiment of the present invention may be rapidly accumulated concentratively in liver cells when infused into the vein, the composition for material delivery may be used to treat a liver disease.

In the present invention, the liver disease may be any one selected from the group consisting of non-alcoholic fatty liver, alcoholic fatty liver, non-alcoholic hepatitis, and alcoholic hepatitis, and may be preferably liver fibrosis or liver cirrhosis.

According to an exemplary embodiment of the present invention, the composition for material delivery may be used to treat arthritis.

The composition for material delivery according to an exemplary embodiment of the present invention may remain in the articular cavity without moving to other organs when infused into the articular cavity. When a drug solution is simply administered to the articular cavity as a method for treating arthritis in the related art, the drug is rapidly discharged from synovial fluid to blood, and thus the medicinal effect does not last for long, but according to an exemplary embodiment of the present invention, the composition for material delivery may remain in the articular cavity for 3 days, 6 days, 8 days, 10 days, or 15 days or more, and thus may be easily used to treat arthritis.

Arthritis is a disease in which inflammation occurs in the joints for various reasons, and according to an exemplary embodiment of the present invention, the arthritis may be osteoarthritis, rheumatoid arthritis, degenerative arthritis, gouty arthritis, infectious arthritis, or lupus arthritis, but is not limited thereto.

According to an exemplary embodiment of the present invention, the composition for material delivery may be used to treat tumors.

The inventors of the present application confirmed that when the composition for material delivery according to an exemplary embodiment of the present invention was infused into a tumor, the composition remained in the tumor without moving to other organs, and since the composition for material delivery may remain in the tumor for, for example, 3 days, 6 days, 8 days, 10 days, 12 days, or 15 days or more, the composition for material delivery may be easily used to treat tumors, preferably cancers which are malignant tumors.

According to an exemplary embodiment of the present invention, the composition for material delivery may be used to label cells. Since the composition for material delivery according to an exemplary embodiment of the present invention includes exosome mimetics derived from red blood cells loaded with a radioactive material and/or fluorescent material and the exosome mimetics derived from red blood cells may be absorbed by cells, it is possible to label cells with the radioactive material and/or fluorescent material via the composition for material delivery.

According to an exemplary embodiment of the present invention, the cells that can be labeled by the composition for material delivery may be white blood cells or cancer cells.

A dosage form of the composition of the present invention may be in a preferred form according to the use method, and in particular, the composition of the present invention may be formulated using a method publicly known in the art so as to provide a rapid, sustained, or delayed release of an active ingredient after being administered to mammals.

The composition of the present invention may be administered parenterally (for example, intravenous, subcutaneous, intraperitoneal, or topical application) according to the intended method, but the administration method is not limited thereto.

According to an exemplary embodiment of the present invention, the composition may further include a carrier, an excipient, or a diluent. The earlier, the excipient, and the diluent may include, for example, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, or mineral oil.

According to an exemplary embodiment of the present invention, the composition may be administered in a pharmaceutically effective amount. In the present invention, "pharmaceutically effective amount" means an amount sufficient to treat a disease at a reasonable benefit/risk ratio applicable to medical treatment, and an effective dosage level may be determined according to factors including type of disease of patients, the severity of disease, the activity of drugs, sensitivity to drugs, administration time, administration route, excretion rate, treatment period, and simultaneously used drugs, and factors well known in other medical fields. The composition may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by the person skilled in the art.

Specifically, according to an exemplary embodiment of the present invention, a preferred dosage of the composition varies depending on the individual's condition and body weight, degree of disease, drug form, administration route and duration, but may be appropriately selected by the person skilled in the art. For example, an amount of about 0.0001 mg/kg to about 100 mg/kg, or about 0.001 mg/kg to about 200 mg/kg may be administered divided once to 24 times daily, once to 7 times per 2 days to 1 week, or once to 24 times per 1 month to 12 months. However, since the preferred dosage may be increased or decreased depending on the administration route, the severity of disease, the gender, the body weight, the age, and the like, the preferred dosage is not intended to limit the scope of the present invention by any method. In the composition, the exosome mimetics derived from red blood cells loaded with the target material may be included in an amount of about 0.0001 wt % to about 10 wt %, or about 0.001 wt % to about 1 wt % based on the total weight of the entire composition.

Another aspect of the present invention provides a method for preparing a composition for material delivery, the method including:

(a) obtaining exosome mimetics derived from red blood cells from red blood cells;

(b) incubating a mixture in which the exosome mimetics derived from red blood cells obtained in step (a) and a target material are mixed;

(c) obtaining a pellet by ultracentrifuging the mixture incubated in step (b); and (d) separating exosome mimetics derived from red blood cells loaded with a target material by washing the pellet obtained in step (c) and using a density gradient.

According to an exemplary embodiment of the present invention, the obtaining of the exosome mimetics derived from red blood cells may be performed by filtering the exosome mimetics derived from red blood cells by a filter, and may be performed by filtering the exosome mimetics derived from red blood cells once to four times by a filter.

According to an exemplary embodiment of the present invention, the ultracentrifuge may be performed at 100,000 g or more, specifically 100,000 g to 200,000 g, or 100,000 g to 150,000 g, or 150,000 g to 200,000 g.

In step (c), a density gradient is a method which is used most frequently when materials having different densities are distinguished, and according to an exemplary embodiment of the present invention, the density gradient may be performed using a density gradient separation material such as ficoll, glycerol, sucrose, cesium chloride, or iodixanol, and the density gradient may be used along with ultracentrifuge, and the like.

According to an exemplary embodiment of the present invention, it is possible to provide a method for preparing a composition for material delivery, in which the target material is one or more selected from the group consisting of a drug, a radioactive material, and a fluorescent material.

According to an exemplary embodiment of the present invention, it is possible to provide a method for preparing a composition for material delivery, the method further including: after step (d), (e) incubating a mixture in which the exosome mimetics derived from red blood cells separated in step (d) and tin (II) chloride are mixed; and (f) adding technetium-99m ($^{99m}Tc$) to the mixture incubated in step (e) and incubating the resulting mixture.

In step (d), $^{99m}Tc$ may be reduced to a low oxidation state where $^{99m}Tc$ is firmly bound to hemoglobin in red blood cells by tin (II) chloride.

According to an exemplary embodiment of the present invention, it is possible to additionally include removing free $^{99m}Tc$ by performing an ultracentrifuge after step (e).

According to an exemplary embodiment of the present invention, by the method for preparing a composition for material delivery, a radiochemical purity meaning a proportion at which exosome mimetics derived from red blood cells are loaded with $^{99m}Tc$, and thus labeled with $^{99m}Tc$ may be 80%, 85%, 90%, 95% or more, or 100%.

According to an exemplary embodiment of the present invention, the exosome mimetics derived from red blood cells loaded with $^{99m}Tc$, which the composition for material delivery includes, are the same as or similar to exosome mimetics derived from red blood cells, which are not loaded with $^{99m}Tc$, in terms of size and morphology.

Still another aspect of the present invention provides a contrast medium including the composition for material delivery.

In the present invention, "contrast medium" means a functional drug which is infused into the stomach, intestinal tract, blood vessels, cerebrospinal cavity, articular cavity, and the like, and thus facilitates distinguishing of tissues or blood vessels during a radiologic examination.

According to an exemplary embodiment of the present invention, since the contrast medium includes exosome mimetics derived from red blood cells loaded with one or more materials selected from the group consisting of a drug, a radioactive material, and a fluorescent material, the contrast medium may be used as an imaging agent and simultaneously may also have a therapeutic effect, and thus, may be used as a therapeutic imaging agent. The therapeutic imaging agent means an imageable therapeutic probe which can treat a disease and simultaneously capture images by imparting an imaging function to a therapeutic medicine, and means a theragnosis enabling therapy and diagnosis at one time.

According to an exemplary embodiment of the present invention, the contrast medium may include labeled cells using the composition for material delivery, and white blood cell may be used as the cells to easily track inflammation.

According to an exemplary embodiment of the present invention, the contrast medium may be applied to nuclear medical imaging.

According to an exemplary embodiment of the present invention, the nuclear medical imaging may be positron emission tomography (PET) or single-photon emission computed tomography (SPECT), or gamma camera imaging.

The contrast medium composition of the present invention may be administered in a parenteral manner. When the contrast medium composition is administered parenterally, the contrast medium composition may be administered via intravenous infusion, intramuscular infusion, intra-articular infusion, intra-synovial infusion, intrathecal infusion, intrahepatic infusion, intralesional infusion, intracranial infusion, or the like.

An adequate dosage of the contrast medium composition of the present invention may vary depending on factors, such as formulation method, administration method, age, body weight, gender or disease condition of the patient, diet, administration time, administration route, excretion rate and response sensitivity.

Further, the contrast medium composition of the present invention may be usefully used to image tissues and diagnose a disease therefrom, and according to an exemplary embodiment of the present invention, the contrast medium composition, comprising white blood cells labeled using by the composition for material delivery loaded with $^{99m}$Tc can be easily used for tracking inflammation. The composition for material delivery according to an exemplary embodiment of the present invention includes exosome mimetics derived from red blood cells, which are capable of being loaded with one or more materials selected from the group consisting of a drug, a radioactive material, and a fluorescent material, and thus can be usefully utilized for a drug carrier, a cell labeling method, a contrast medium, and the like, and treatment and diagnosis can be simultaneously performed using the composition for material delivery according to an exemplary embodiment of the present invention.

In addition, since the exosome mimetics derived from red blood cells, which the material composition according to an exemplary embodiment of the present invention includes, are accumulated in the liver in vivo and remain in the articular cavity or tumor during infusion into the articular cavity or tumor, the material composition according to an exemplary embodiment of the present invention can be used to treat a liver disease, arthritis, and a tumor.

BRIEF DESCRIPTION OF THE DRAWINGS

In FIG. 10, the upper graph illustrates the radiation dose measured from different organs, specifically illustrating the radiation dose measured in division to the lower left panel and right panel.

FIG. 11A illustrates a fluorescent image of RBC-EM$^{DiD}$ in vivo. FIG. 11B illustrates a fluorescent image (left image) of RBC-EM$^{DiD}$ in the liver and spleen collected from mice and a result (right graph) of quantifying the same.

FIG. 12A illustrates an immunofluorescence assay image on RBC-EM$^{DiD}$ in the section of a liver tissue, and FIG. 12B illustrates fluorescence values observed in the immunofluorescence assay of CD68+(left graph) and DiD (right graph).

FIGS. 16A to 16D illustrate that in an acute inflammation mouse model, white blood cells labeled with $^{99m}$Tc may be effectively used to track inflammation. Specifically, FIG. 16A illustrates a gamma camera image in an acute inflammation mouse model into which $^{99m}$Tc-WBC is infused via the tail vein. FIG. 16B illustrates amounts of radiation measured from the left and right feet of the acute inflammation mouse model to which $^{99m}$Tc-WBC is injected. FIG. 16C illustrates the biodistribution of $^{99m}$Tc-WBC. FIG. 16D illustrates the amounts of $^{99m}$Tc-WBC taken up by the left and right feet.

FIG. 17A illustrates a gamma camera image of mice with rheumatoid arthritis, and FIG. 17B quantitatively illustrates amounts of measured radiation. The left graph of FIG. 17B illustrates absolute values of amounts of radiation measured (background corrected counts) in a portion injected into the arthritic lesion, and the right graph illustrates the amounts of radiation (retention rate) remaining in the injected lesion after radiation decay correction in the same data.

As a result of performing fluorescent imaging after $^{99m}$Tc-DiD-RBC-EM is infused into the articular cavity of the animal model with rheumatoid arthritis.

DETAILED DESCRIPTION

Hereinafter, the present invention will be described in more detail through the Examples. However, these Examples are provided only for exemplarily explaining the present invention, and the scope of the present invention is not limited by these Examples.

Example 1. Preparation of Exosome Mimetics Derived from Red Blood Cells 1-1. Preparation of Exosomes Derived From Red Blood Cells (RBC-Exo) and Exosome Mimetics (RBC-EM) Derived From Red Blood Cells (RBC-EM)

Blood samples were collected from Sprague Dawley rats (150 g; 6 weeks old; Hana Corp., Korea) in the presence of a citrate-dextrose solution (Sigma-Aldrich, USA) as an anticoagulant.

The collected blood was centrifuged at 200 g at 18° C. to 22° C. for 15 min to 20 min. A buffy coat of a blood supernatant was obtained from the top of concentrated red blood cells (packed RBCs), and the same was used to separate red blood cells. Subsequently, the concentrated red blood cells were collected. The red blood cells (RBCs) were obtained by a one-time centrifugation step under the conditions of 1,500 g at 4° C. for 20 min.

Exosomes were obtained from red blood cells by a previously publicly known method (Varga et al., Cancer Biother. Radiopharm. 31, 168-173, 2016), and exosomes derived from red blood cells were named as RBC-Exo.

Red blood cells (RBC) were diluted by adding PBS to red blood cells (RBC:PBS=1:9 volume ratio), and the diluted red blood cells were extruded by a 1-μm pore size polycarbonate membrane filter (Nuclepore, Whatman, Inc., Clifton, N.J., USA) once to four times using a mini-extruder (Vanti Polar Lipids, Birmingham, Ala., USA). The extruded sample was diluted by adding 20×PBS to the sample, and centrifuged at 3,000 g for 10 min in order to remove RBC, larger vesicles, and debris. The centrifuged sample was filtered by a 0.22 μm syringe filter, and ultra-centrifuged (Beckman Coulter, CA, USA) at 4° C. and 100,000 g for 1 hour. After the ultracentrifugation, a two-step density gradient ultracentrifugation was performed at 4° C. using iodixanol (OptiPrep™ Density Gradient Medium, Sigma-Aldrich, USA). The exosome mimetics derived from red blood cells were obtained at the intersection point of a 60% iodixanol layer and a 20% iodixanol layer, and were immediately used without an additional treatment. The obtained exosome mimetics derived from red blood cells were named as RBC-exosome mimetics (RBC-EM).

Figure 1:
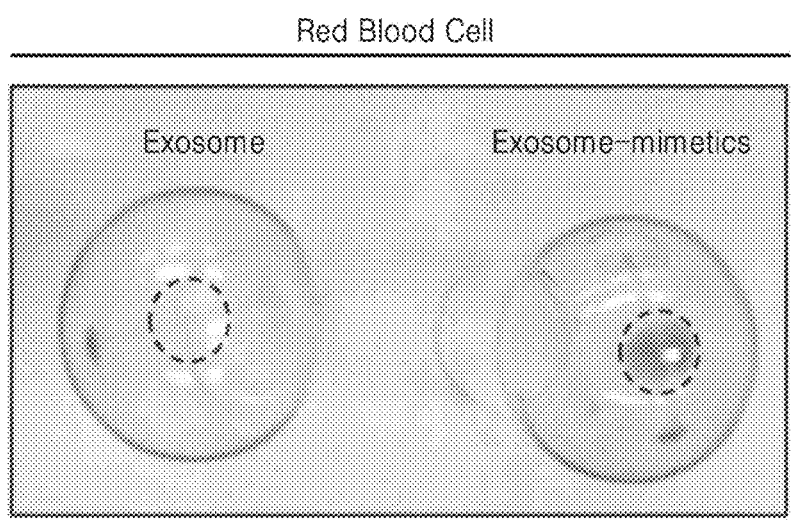
FIG. 1 illustrates a visual image of exosome derived from red blood cells (RBC-Exo) and exosome mimetics derived from red blood cells (RBC-EM), which are prepared from the same number of red blood cells.

FIG. 1 illustrates a visual image of RBC-Exo and RBC-EM, which are prepared from the same number of red blood cells. The dotted line of FIG. 1 indicates the positions of RBC-Exo and RBC-EM. As illustrated in FIG. 1, it can be confirmed that the number of RBC-EM is larger than that of naturally-derived RBC-Exo.

1-2. Analysis of Numbers of RBC-Exo and RBC-EM and Protein Amounts

Figure 2A:
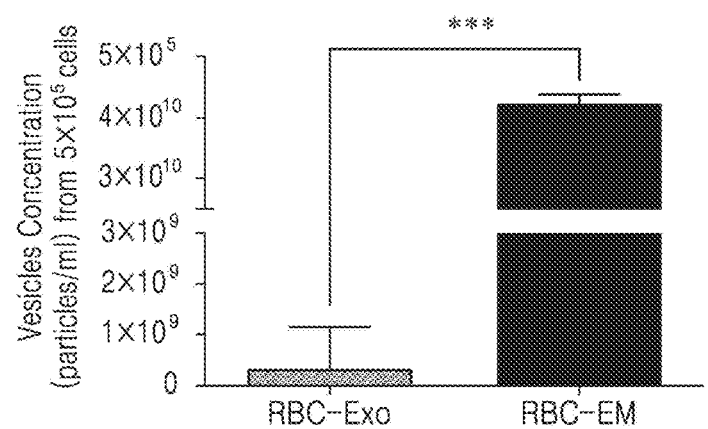
FIG. 2A illustrates the concentrations (number prepared/ml) of RBC-Exo and RBC-EM, which are prepared from the same number of red blood cells.

By ultracentrifugation and extraction methods, the numbers of RBC-Exo and RBC-EM produced from $5\times10^6$ red blood cells (RBCs) were determined. FIG. 2A illustrates the concentrations (number prepared/ml) of RBC-Exo and RBC-EM, which are prepared from the same number of red blood cells. As illustrated in FIG. 2A, the number of RBC-EM prepared from the same number of red blood cells was about 130-times larger than the number of RBC-Exo prepared from the same number of red blood cells ($P<0.001$).

Figure 2B:
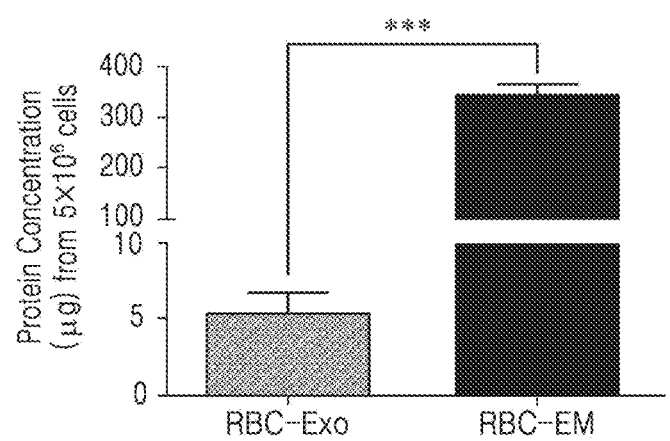
FIG. 2B illustrates the total protein contents of RBC-Exo and RBC-EM, which are prepared from the same number of red blood cells.

The protein amounts of RBC-Exo and RBC-EM were measured by a previously publicly known method (Gangadaran et al., Oncotarget 8, 109894-109914, 2017). FIG. 2B illustrates the total protein contents of RBC-Exo and RBC-EM, which are prepared from the same number of red blood cells. As illustrated in FIG. 2B, RBC-EM prepared from the same number of red blood cells showed a significantly higher protein concentration (about 65 times) than that of RBC-Exo ($P<0.001$).

From the result, it can be seen that RBC-EM can be mass-produced more efficiently than naturally made RBC-Exo.

Example 2. Labeling of Exosome Mimetics Derived From Red Blood Cells (RBC-EM) With $^{99m}$Tc and Labeling Purity 2-1. Labeling Exosome Mimetics Derived From Red Blood Cells (RBC-EM) With $^{99m}$Tc Since only $^{99m}$Tc reduced to a low oxidation state is firmly bound to hemoglobin, particularly, the beta-chain of hemoglobin, RBC-EM was incubated along with tin (II) chloride in order to reduce $^{99m}$Tc. The RBC-EM obtained in Example 1-1 and the same amount of 0.01% tin (II) chloride (Sigma, USA) were incubated in a shaker at 37° C. for 5 min, and the exosome mimetics derived from red blood cells were labeled with a radioactive material ($^{99m}$Tc) by adding technetium-99m ($^{99m}$Tc) to RBC-EM (RBC-EM (100 μg): $^{99m}$Tc (111 MBq)) and incubating the resulting mixture in a shaker at 37° C. for 20 min, and the labeled exosome mimetics derived from red blood cells were named as $^{99m}$Tc-RBC-EM. When a radiochemical purity was less than 95%, an ultracentrifugation was performed at 4° C. and 100,000 g for 1 hour in order to purify $^{99m}$Tc-RBC-EM.

Figure 3:
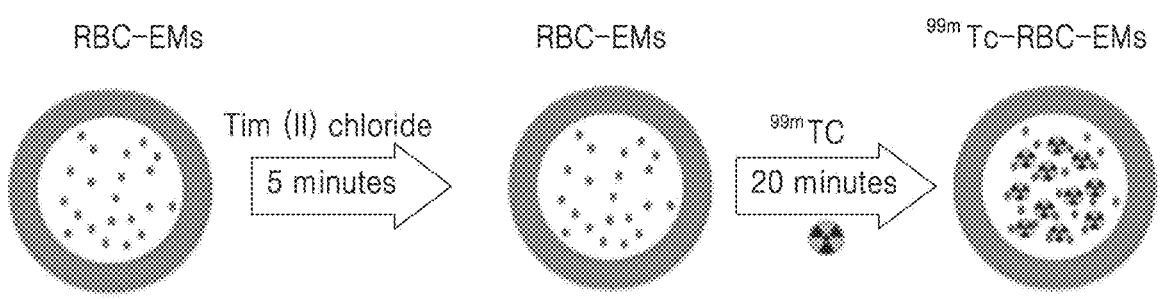
FIG. 3 is a schematic view schematically illustrating a process of labeling RBC-EM with $^{99m}$Tc.

FIG. 3 is a schematic view schematically illustrating a process of labeling RBC-EM with $^{99m}$Tc.

2-2. $^{99m}$Tc Labeling Purity

The labeling purity of RBC-EM with $^{99m}$Tc was measured using instant thin-layer chromatography (TLC) using a 0.9% NaCl solution as each column eluent, and the radioactivity of the column was counted using a radio-TLC imaging scanner (AR-2000, Bioscan, Poway, Calif., United States). The stability was determined by a rate of change in radiochemical purity of $^{99m}$Tc-RBC-EM according to the passage of time.

Figure 4:
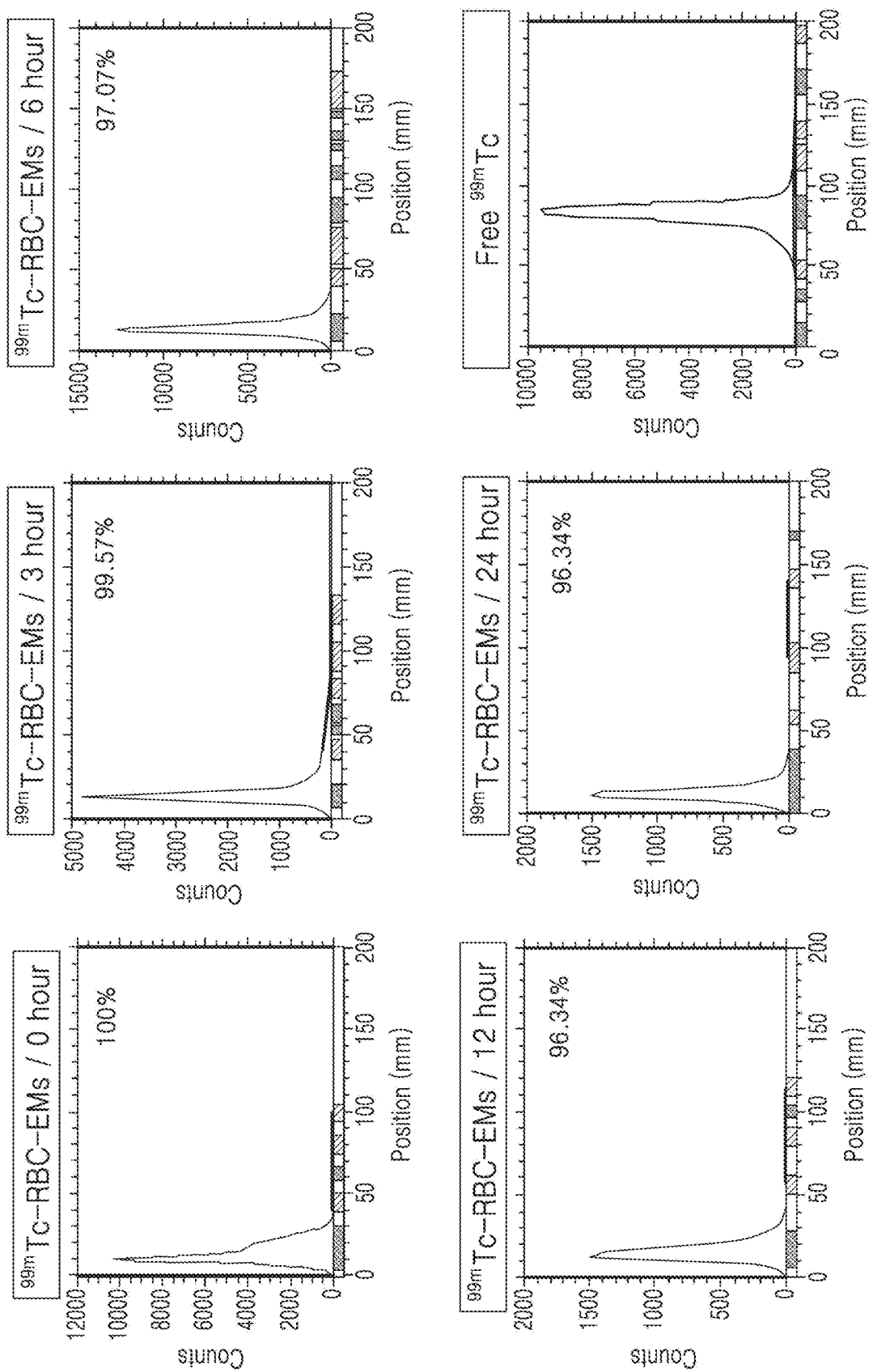
FIG. 4 illustrates a radiochemical purity of exosome mimetics derived from red blood cells labeled with $^{99m}$Tc ($^{99m}$Tc-RBC-EM) over time.

FIG. 4 illustrates the radiochemical purity of $^{99m}$Tc-RBC-EM over time. As illustrated in FIG. 4, the radiochemical purity immediately after purification by ultracentrifugation (0 hour) was 100%. The proportion of RBC-EM labeled with $^{99m}$Tc was 99.57% (3 hours), 97.07% (6 hours), 96.34% (12 hours), and 94.98% (24 hours). The radiochemical purity was analyzed by employing free $^{99m}$Tc as a control.

Through the aforementioned result, it can be seen that exosome mimetics derived from red blood cells ($^{99m}$Tc-RBC-EM) labeled with $^{99m}$Tc as a radioactive material were stable.

2-3. Measurement of Serum Stability $^{99m}$Tc-RBC-EM was cultured in a PBS solution including 20% FBS in a $CO_2$ incubator at 37° C. The stability of $^{99m}$Tc-RBC-EM was measured in 0, 1, 3, and 24 hours after the culture using a radio-TLC imaging scanner (AR-2000, Bioscan, Poway, Calif., United States).

Figure 5:
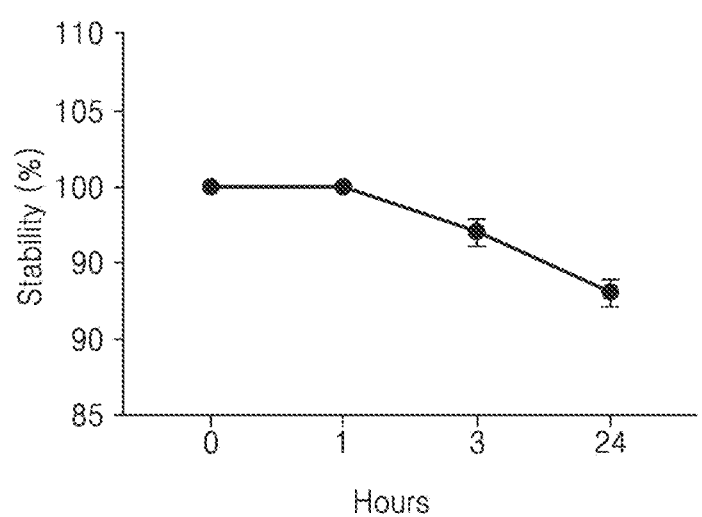
FIG. 5 illustrates the stability of $^{99m}$Tc-RBC-EM over time.

FIG. 5 illustrates the stability of $^{99m}$Tc-RBC-EM over time. As illustrated in FIG. 5, it can be seen that $^{99m}$Tc-RBC-EM is stable up to 24 hours.

Example 3. Analysis of Characteristics of RBC-EM and $^{99m}$Tc-RBC-EM 3-1. Nanoparticle Tracking Analysis (NTA)

Particle sizes of RBC-Exo and RBC-EM prepared by the method in Example 1-1 and $^{99m}$Tc-RBC-EM prepared by the method in Example 2-1 were analyzed using Nano Sight LM 10 (Malver) according to the provided protocol. Each sample was diluted 1000 times with Milli-Q water and infused into a chamber using a sterilized syringe, and measurement was performed in the same manner as the previously publicly known method (Gangadaran et al., J. Control. Release 264, 112-126, 2017).

3-2. Field Emission Transmission Electron Microscopy (FE-TEM) and Scanning Transmission Electron Microscopy (STEM)

Pellets of RBC-Exo, RBC-EM, and $^{99m}$Tc-RBC-EM samples were resuspended in 100 μl of 2% paraformaldehyde. 5 μl of each sample was attached (drop) to a formvar/carbon-coated EM grid (Electron Microscopy Sciences, USA), and dried in an open space for 20 min. For washing, 50 μl of PBS was added to a parafilm sheet, and the grid was floated upside down on the PBS balls using sterilized forceps. The grid was transferred to 50 μl of 1% glutaraldehyde, incubated for 5 min and washed with distilled water for 2 min. RBC-EM and $^{99m}$Tc-RBC-EM on the grid were stained with 10 μl of 2% uranyl acetate, and then the grid was again washed 7 times with PBS. Thereafter, the grid was completely dried. All the processes were performed at room temperature.

In order to observe the sizes of RBC-Exo, RBC-EM, and $^{99m}$Tc-RBC-EM and perform an element analysis, the sample was observed in a Titan G2 ChemiSTEM (FEI Company) with a Cs Probe (FEI company, Netherlands). In order to measure the sizes of RBC-Exo, RBC-EM, and $^{99m}$Tc-RBC-EM, a HT 7700 transmission electron microscope (Hitachi, Tokyo, Japan) was used.

3-3. Characteristics of RBC-EM and $^{99m}$Tc-RBC-EM

Figure 6A:
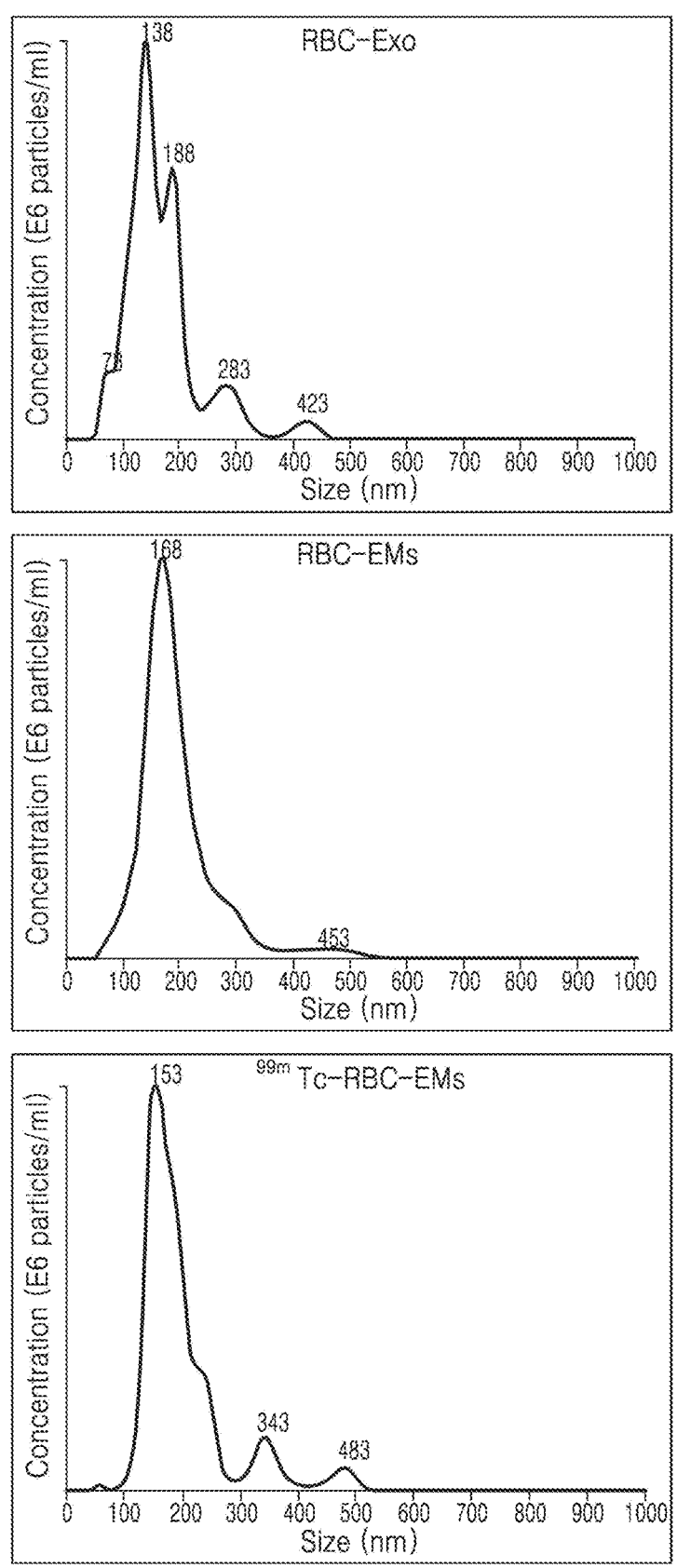
FIG. 6A illustrates the size distribution of RBC-Exo, RBC-EM, and $^{99m}$Tc-RBC-EM.
Figure 6B:
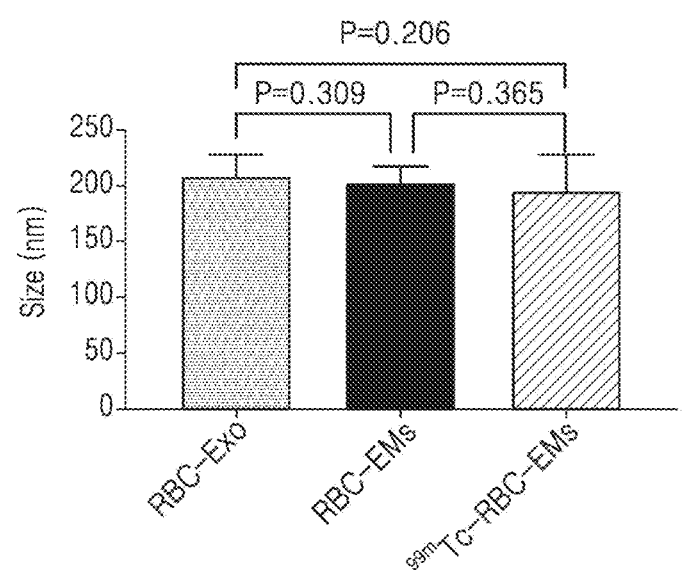
FIG. 6B illustrates the average sizes of RBC-Exo, RBC-EM, and $^{99m}$Tc-RBC-EM.

The size distribution of RBC-Exo, RBC-EM, and $^{99m}$Tc-RBC-EM was measured by the method in Example 3-1. FIG. 6A illustrates the size distribution of RBC-Exo, RBC-EM, and $^{99m}$Tc-RBC-EM, and FIG. 6B illustrates the average sizes of RBC-Exo, RBC-EM, and $^{99m}$Tc-RBC-EM. As illustrated in FIG. 6, as a result of NTA analysis, the size of RBC-Exo was within a range of 30 nm to 450 nm, and the average size thereof was 209.1±19.8 nm. Further, the unlabeled RBC-EM had an average diameter of 201.3±16 nm, and $^{99m}$Tc-RBC-EM labeled with $^{99m}$Tc had an average diameter of 195.0±11.1 nm. The sizes of RBC-Exo, RBC-EM, and $^{99m}$Tc-RBC-EM did not show a significant difference (all the P values were 0.05 or more).

From this, it can be seen that the size of the exosome mimetics derived from red blood cells is similar to that of red blood exosomes, and the change in size was not generated by a $^{99m}$Tc radioactive label.

Figure 7:
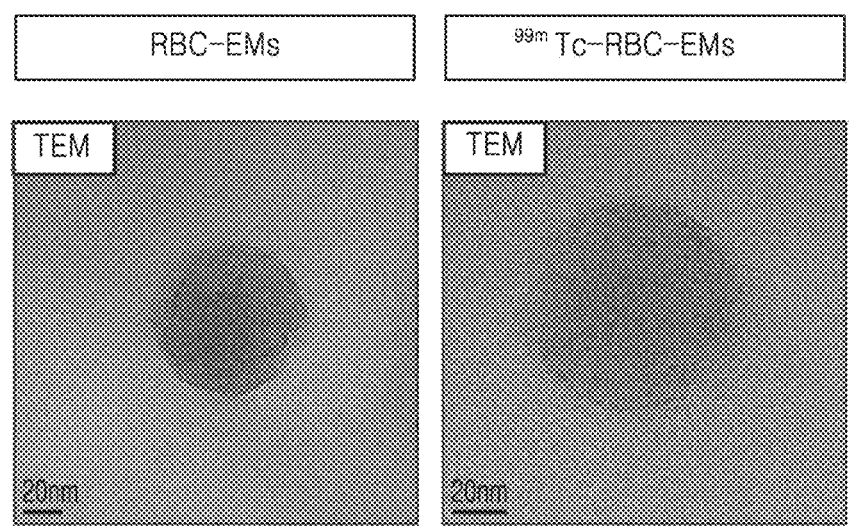
FIG. 7 illustrates an image in which RBC-EM and $^{99m}$Tc-RBC-EM are observed by field emission transmission electron microscopy (FE-TEM).

In order to confirm whether the radioactive label changed the shape and morphology of RBC-EM and analyze whether $^{99m}$Tc was present therein or in the membrane, FE-TEM was performed by the method in Example 3-2. FIG. 7 illustrates an image in which RBC-EM and $^{99m}$Tc-RBC-EM are observed by field emission transmission electron microscopy (FE-TEM). As illustrated in FIG. 7, it was confirmed that there was no morphological change caused by the $^{99m}$Tc label because both the unlabeled RBC-EM and $^{99m}$Tc-RBC-EM maintained a similar circular shape.

The aforementioned result shows that the radioactive label of $^{99m}$Tc does not change the size and shape of RBC-EM.

Figure 8:
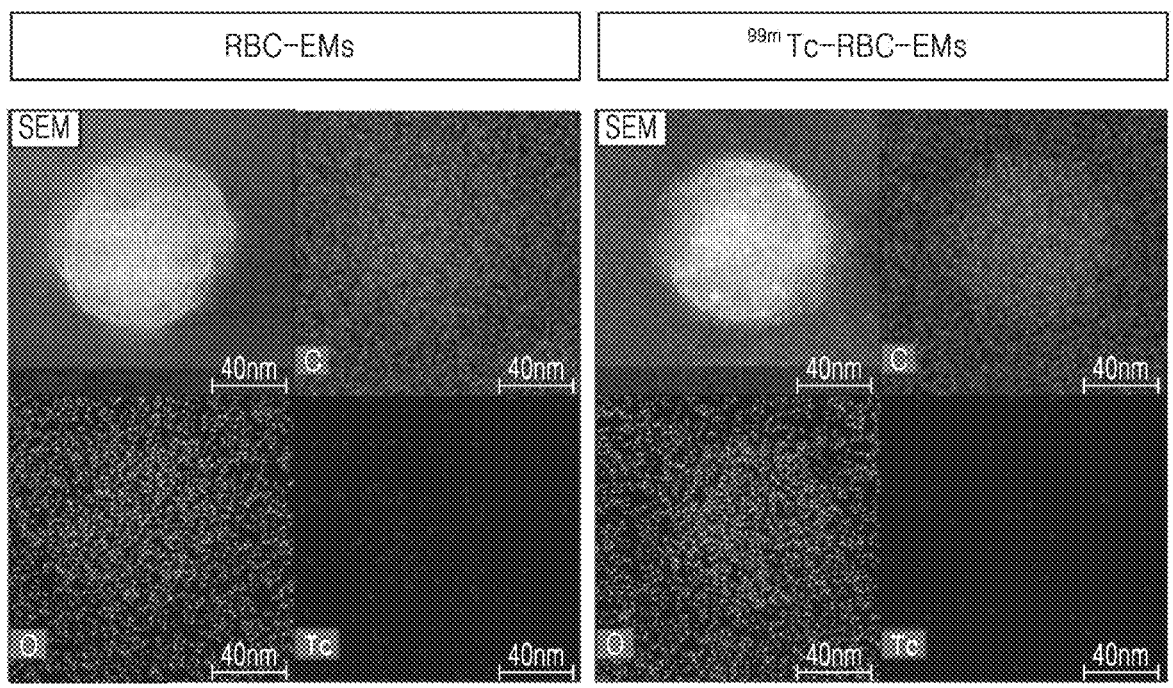
FIG. 8 illustrates an image in which RBC-EM and $^{99m}$Tc-RBC-EM are observed by high-angle annular dark field scanning transmission electron microscopy (HAADF-STEM).

FIG. 8 illustrates an image in which RBC-EM and $^{99m}$Tc-RBC-EM were observed by high-angle annular dark field scanning transmission electron microscopy (HAADF-STEM). Table 1 shows the results of quantifying the amounts of iron and technetium present in the cytosol of RBC-EM and $^{99m}$Tc-RBC-EM using the STEM image of FIG. 8. As in the results of Table 1 and FIG. 8, it can be seen that $^{99m}$Tc is successfully included in the inside (cytosol) of RBC-EM because $^{99m}$Tc is significantly abundantly present in the cytosol of $^{99m}$Tc-RBC-EM.

TABLE 1

|  | RBC-EM | | $^{99m}$Tc-RBC-EM | |
| --- | --- | --- | --- | --- |
|  | Weight (wt). % | Error in wt. % | Weight (wt). % | Error in wt. % |
| Iron | 90.17 | 21.94 | 40.80 | 18.89 |
| Technetium | 9.92 | 9.53 | 59.20 | 34.59 |

4. In Vivo Distribution of $^{99m}$Tc-RBC-EM 4-1. In Vivo Gamma Camera Imaging

In vivo gamma camera imaging was performed on 5-week-old male C57BL/6 mice (Hamamatsu, Shizuoka). The gamma camera images were captured and taken for 10 min using a 2 mm pinhole collimator (Infinia II, GE Healthcare, Milwaukee, Wis., USA). A 200 μl volume of 37 MBq $^{99m}$TC-RBC-EM was infused into the tail vein of mice. As a control, the same amount of free $^{99m}$Tc was infused. During the imaging, mice were continuously anesthetized using 2.5% isoflurane (Merial, Lyon, France). The gamma camera images were obtained by capturing the gamma camera images 1 hour and 3 hours after infusing $^{99m}$Tc-RBC-EM and free $^{99m}$Tc.

The region of interests (ROIs) in mice into which free $^{99m}$Tc was infused were the thyroid gland and the stomach, and the region of interests (ROIs) in mice into which $^{99m}$Tc-RBC-EM was infused were the thyroid gland and the liver/spleen. The right thigh part was used as a control of ROI. The average ROI count per pixel was calculated by dividing the same mice by the control ROI.

Figure 9A:
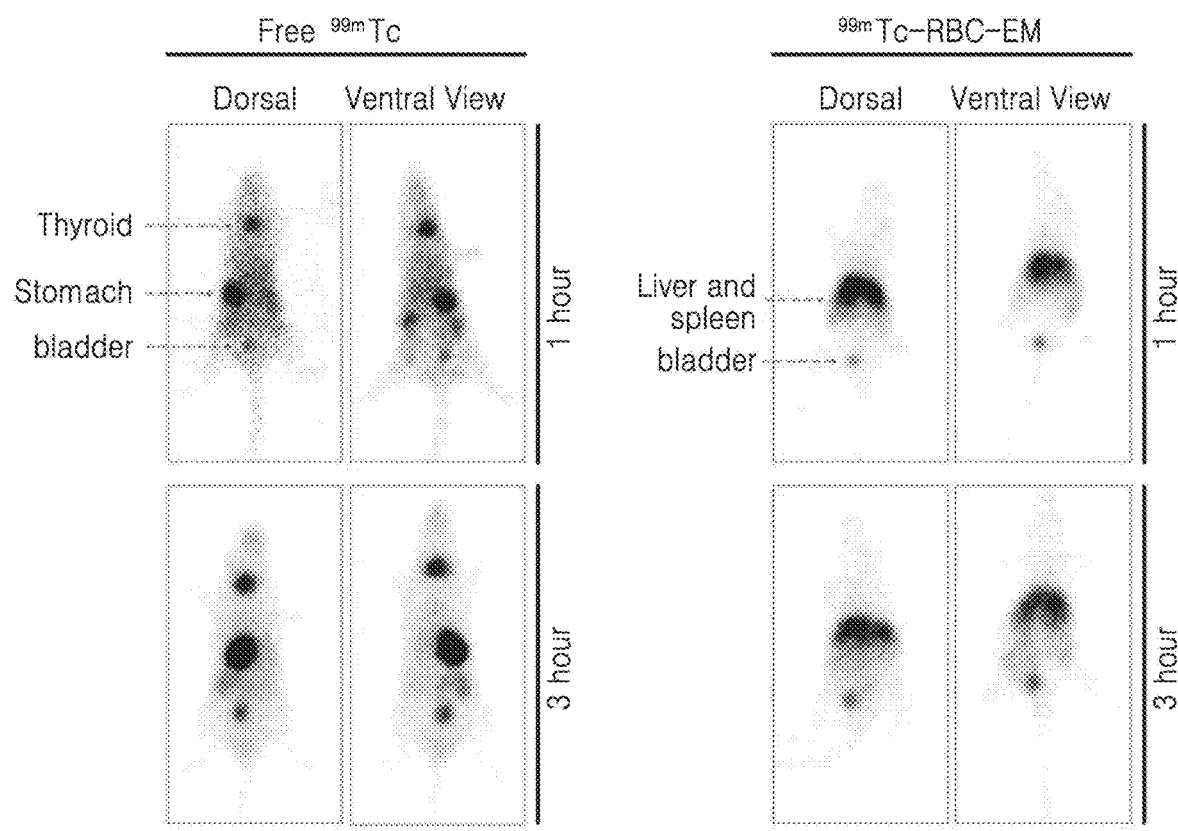
FIG. 9A illustrates an in vivo gamma camera image of free $^{99m}$Tc and $^{99m}$Tc-RBC-EM.
Figure 9B:
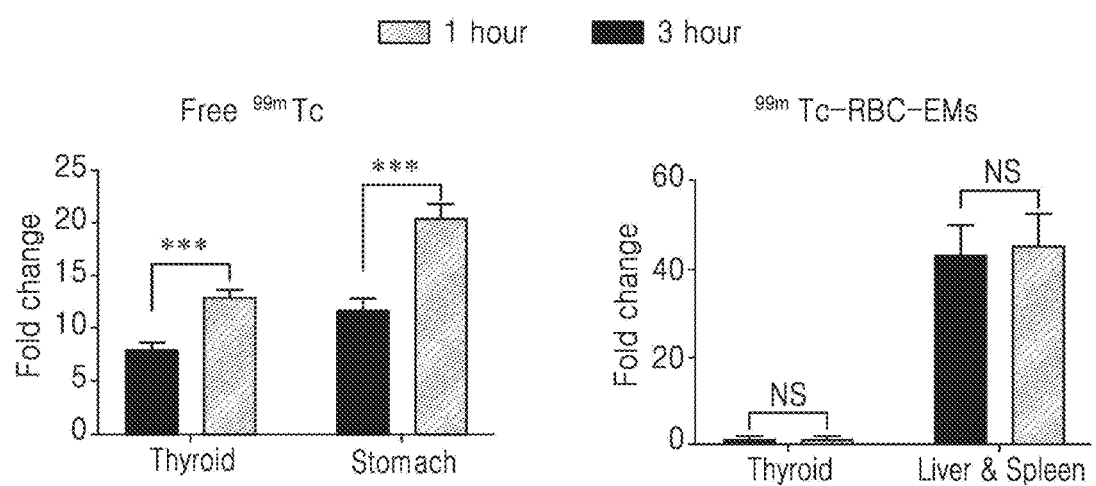
FIG. 9B illustrates quantitative values of the measured radiation.

After $^{99m}$Tc and $^{99m}$Tc-RBC-EM were injected into the vein of mice, the in vivo gamma camera images were obtained. FIG. 9A illustrates an in vivo gamma camera image of free $^{99m}$Tc and $^{99m}$Tc-RBC-EM, and FIG. 9B illustrates quantitative values of the measured radiation. As illustrated in FIG. 9, the in vivo gamma camera images show that $^{99m}$Tc-RBC-EM may be clearly detected from living mice. The image obtained 1 hour after injecting free $^{99m}$Tc shows a strong uptake of free $^{99m}$Tc in the thyroid gland, the stomach, and the bladder (left upper panel of FIG. 9A). Simultaneously, the uptake of $^{99m}$Tc-RBC-EM was obtained in the liver, the spleen, and the bladder 1 hour after injecting $^{99m}$Tc-RBC-EM (right upper panel of FIG. 9A). Unlike free $^{99m}$Tc, the absorption of $^{99m}$Tc-RBC-EM in the thyroid gland or stomach of mice was not observed. Further, the gamma camera image 3 hours after the infusion showed a pattern similar to the image captured 1 hour after the infusion (right lower and left lower panels of FIG. 9A). However, the absorption of free $^{99m}$Tc in the thyroid gland and the stomach was significantly (P<0.001) increased 3 hours after the infusion compared to that 1 hour after the infusion (left graph of FIG. 9B), whereas the uptake of $^{99m}$Tc-RBC-EM in the thyroid gland, the liver, and the spleen 3 hours after the infusion was not significantly increased (P>0.05) compared to that 1 hour after the infusion (right graph of FIG. 9B).

Free $^{99m}$Tc is easily taken up by the thyroid gland and the stomach due to chemical characteristics via different mechanisms. However, for $^{99m}$Tc-RBC-EM, since $^{99m}$Tc is bound to hemoglobin (Hb) present in the cytosol of RBC-EM, radiation may be detected by $^{99m}$Tc, but $^{99m}$Tc-RBC-EM behaves in vivo as characteristics of RBC-EM. Accordingly, RBC-EM is taken up by the reticuloendothelial system such as the liver or the spleen. As illustrated in FIG. 9B, since the uptake of $^{99m}$Tc-RBC-EM in the thyroid gland was not increased even 3 hours after the infusion likewise 1 hour after the infusion, it means that free $^{99m}$Tc freed from $^{99m}$Tc-RBC-EM is scarcely present up to 3 hours, and through this, it can be seen that the bond of $^{99m}$Tc and RBC-EM is stable.

4-2. Biodistribution of $^{99m}$Tc-RBC-EM $^{99m}$TC-RBC-EM or free $^{99m}$TC was infused into mice via intravenous injection. One hour later, blood samples were collected, and the mice were sacrificed. The uptake value was measured using a gamma counter in the organ such as the lungs, the heart, the liver, the stomach, the spleen, the intestines, the kidneys, the muscle, and the thyroid gland. The resulting values were expressed as a percentage of the amount injected per gram of tissue (% ID/g).

Figure 10:
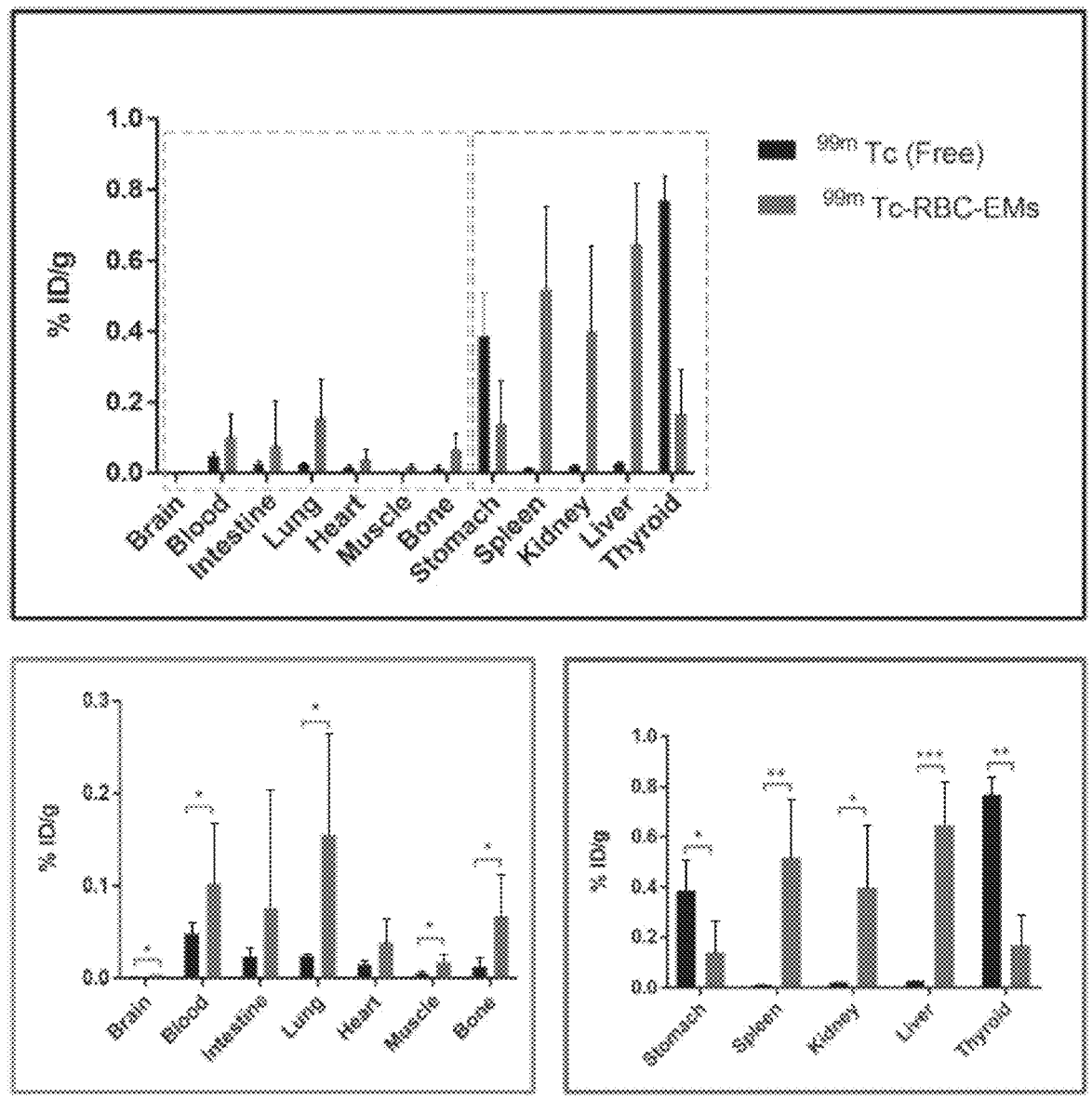
FIG. 10 illustrates results of measuring the biodistribution of $^{99m}$Tc and $^{99m}$Tc-RBC-EM after free $^{99m}$Tc and $^{99m}$Tc-RBC-EM are administered to mice via intravenous injection.

FIG. 10 illustrates results of measuring the biodistribution of $^{99m}$Tc and $^{99m}$Tc-RBC-EM after free $^{99m}$Tc and $^{99m}$Tc-RBC-EM are administered to mice via intravenous injection. In FIG. 10, the upper graph illustrates the radiation dose measured from different organs, specifically illustrating the radiation dose measured in the lower left panel and right panel. As illustrated in FIG. 10, the absorption of $^{99m}$Tc-RBC-EM in the thyroid gland was low similarly (P<0.01) compared to that of free $^{99m}$Tc. A similar uptake tendency was also observed from the stomach (P<0.05). The absorption of $^{99m}$Tc-RBC-EM in the liver (P<0.001), the spleen (P<0.01), and the kidneys (P<0.05) was 20 to 40 times higher than the uptake of free $^{99m}$Tc in these organs. Further, as illustrated in FIG. 10, the absorption of $^{99m}$Tc-RBC-EM in the brain (P<0.05), the blood (P<0.05), the lungs (P<0.05), the muscle (P<0.05), and the bones (P<0.05) is also higher than that of free $^{99m}$Tc. These results show that exosome mimetics derived from red blood cells labeled with a radioactive material ($^{99m}$Tc-RBC-EM) may be visualized in living animals.

4-3. Fluorescent Imaging of RBC-EM DID In Vivo and Ex Vivo

After RBC-EM and 1,1'-dioctadecyl-3,3,3',3'-tetramethylindodicarbocyanine perchlorate (DiD; Thermo Fisher Scientific) were cultured together at room temperature for 20 min, the cultured product was washed with PBS, and RBC-EM$^{DiD}$ was separated by performing a two-step Opti-Prep density gradient ultracentrifugation in the same manner as in Example 1-1. C57BL/6 mice were anesthetized with isoflurane, and RBC-EM$^{DiD}$ or PBS was infused into the tail vein via intravenous injection. 1 minute and 1 hour after the infusion, fluorescent imaging was performed using an in vivo imaging system (IVIS Lumina III instrument, PerkinElmer) [wavelengths: Excitation—644 nm and emission—665 nm; imaging parameters: binning—4, smoothing—3×3, Field of subject(stage—D): 12.5 cm, height of subject image: 1.5 cm]. Ex vivo fluorescent imaging was performed by collecting the liver and spleen after the imaging, and a quantitative analysis was performed using IVIS software (Living Image Software, PerkinElmer).

Figure 11A:
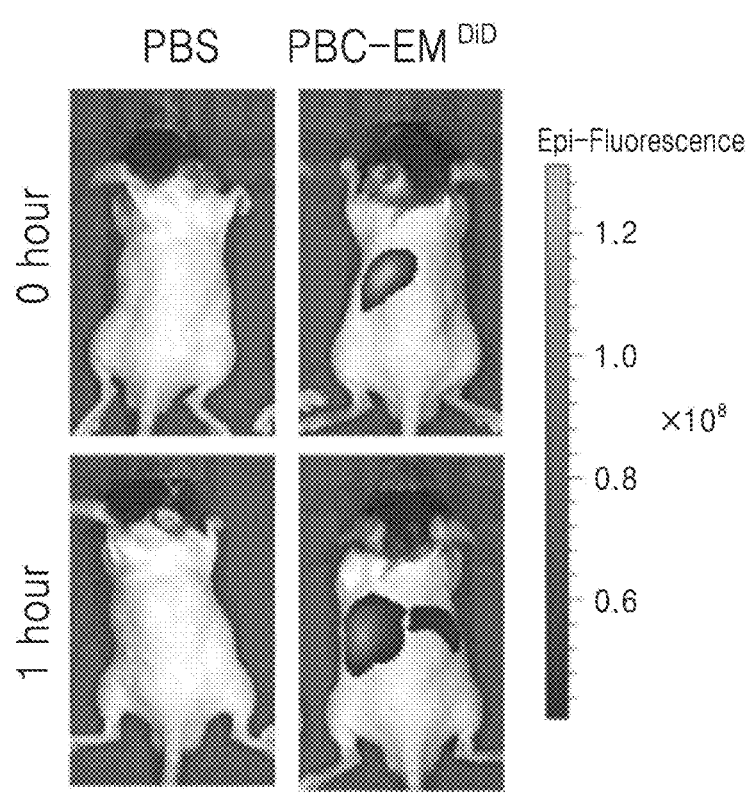
FIG. 11A and FIG. 11B illustrate the results in which fluorescent imaging is performed on RBC-EM$^{DiD}$. Specifically.
Figure 11B:
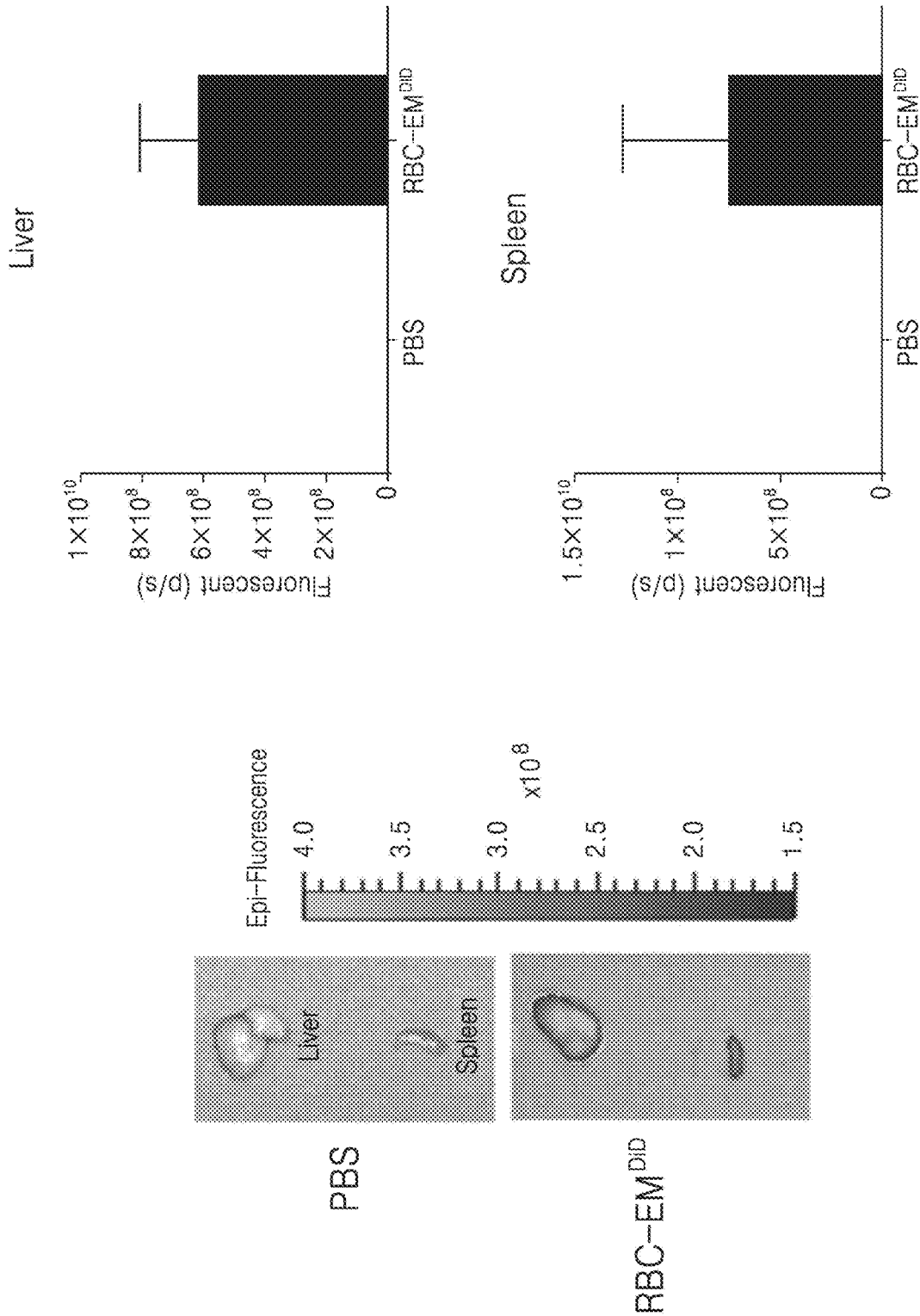

In order to examine the biodistribution of RBC-EM, RBC-EM was labeled with DiD by the aforementioned method, and then administered intravenously to the mice. FIG. 11A and FIG. 11B illustrate the results in which fluorescent imaging is performed on RBC-EM$^{DiD}$. Specifically, FIG. 11A illustrates a fluorescent image of RBC-EM$^{DiD}$ in vivo. FIG. 11B illustrates a fluorescent image of RBC-EM$^{DiD}$ in the liver and spleen collected from mice and a result of quantifying the same. As illustrated in the drawing, immediately after the administration (0 hour), a strong fluorescent signal was shown in the liver, and 1 hour after the administration, stronger fluorescent signals were shown in the regions of the liver and spleen. In contrast, as illustrated in FIG. 11A, the control (administration of PBS) mice did not show any signal. As illustrated in FIG. 11B, it can be seen that RBC-EM$^{DiD}$ is significantly distributed in the liver and spleen through in vivo and ex vivo fluorescent imaging.

4-4. Immunofluorescence Assay

In order to analyze the location of RBC-EM in more detail, the liver tissue was cryo-sectioned and subjected to immunofluorescence (IF) assay. The liver sections of mice into which RBC-EM$^{DiD}$ or PBS was infused were stained with anti-rabbit CD68 (Abcam), and then stained with goat anti-rabbit FITC (Abcam). The liver tissues were mounted using a VECTASHIELD mounting medium (Vector Laboratories, Burlingame, Calif., United States). The immunofluorescence (IF)-stained sections were observed under a confocal microscope (LSM 5 Exciter, Zeiss, Oberkochen, Germany). The observer counted 6 fields. The number of CD68 positive (CD68+; green) cells were counted from RBC-EM$^{DiD}$ or PBS-infused mouse liver sections. And then, DiD positive was counted from CD68+ or CD68− cells.

Figure 12A:
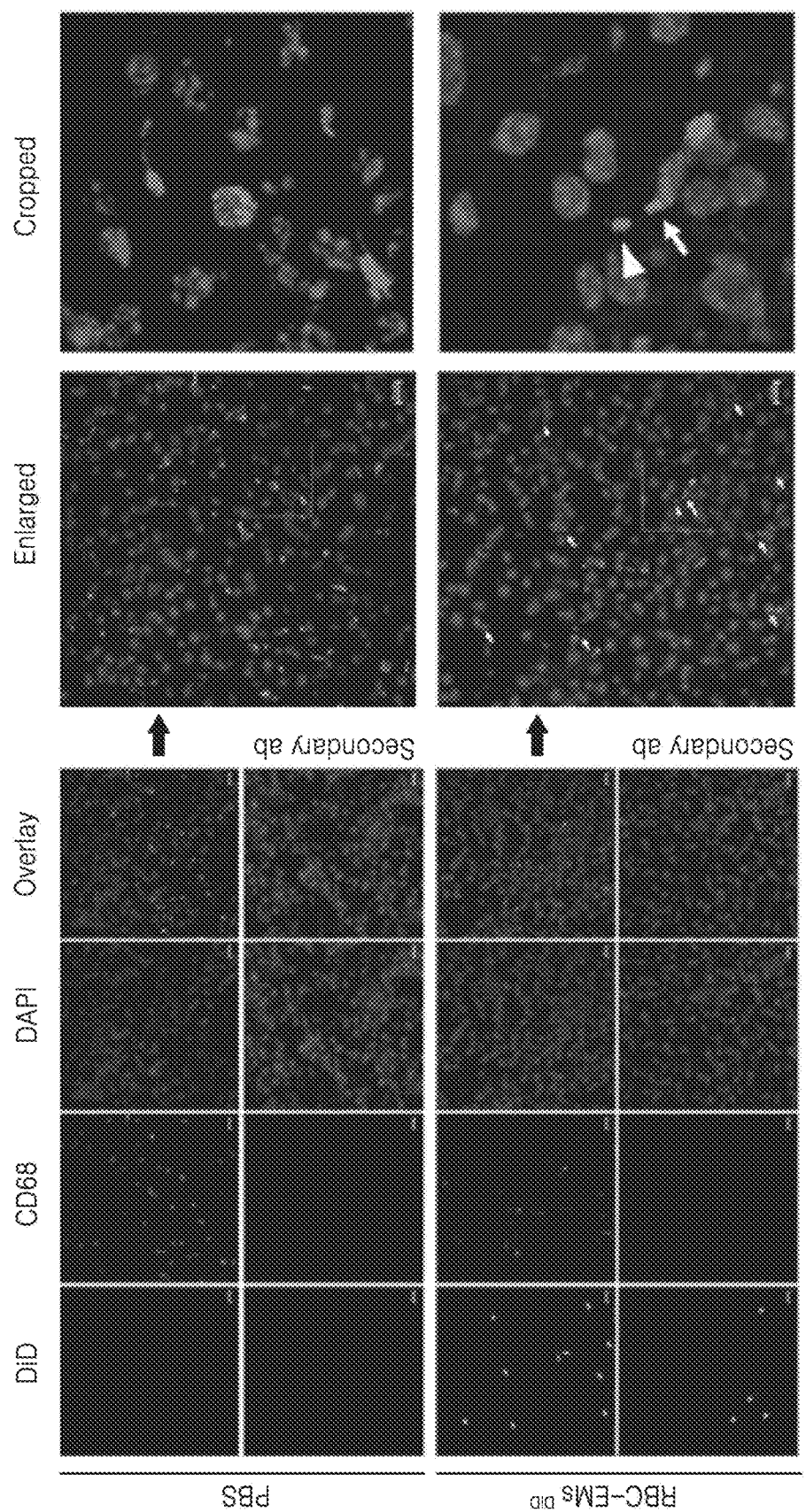
FIG. 12A and FIG. 12B illustrate the results of performing an immunofluorescence assay on RBC-EM$^{DiD}$ in the section of a liver tissue. Specifically.
Figure 12B:
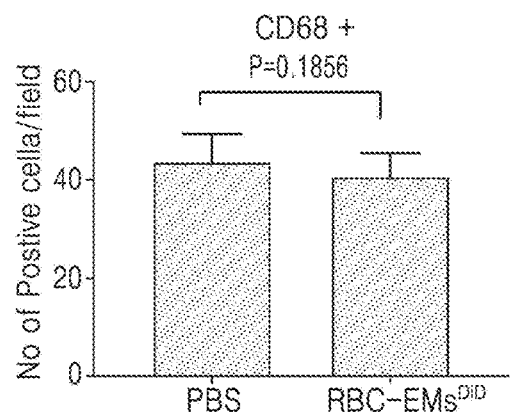
Figure 12B:
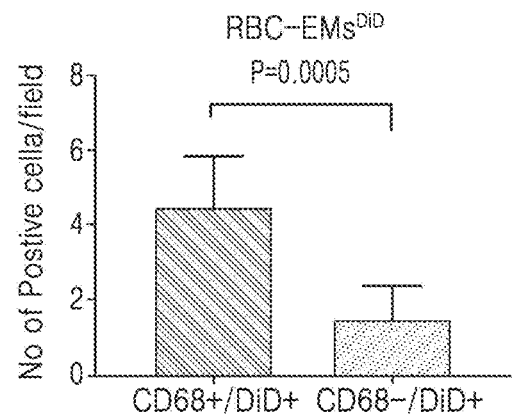

FIG. 12A and FIG. 12B illustrate the results of performing an immunofluorescence assay on RBC-EM$^{DiD}$ in the section of a liver tissue. Specifically, FIG. 12A illustrates an immunofluorescence assay image on RBC-EM$^{DiD}$ in the section of a liver tissue, and FIG. 12B illustrates immunofluorescence results for CD68+ and DiD with numerical values. As illustrated in the drawing, it was confirmed that there was no significant (P=0.1856) change in CD68 positive cells (Kupffer cells, liver resident macrophages) in the liver section. Further, as a result of immunofluorescence assay, it can be seen that a considerable number of RBC-EM$^{DiD}$ coexist with Kupffer cells. As illustrated in the drawing, about 75% of RBC-Em$^{DiD}$ were restricted to Kupffer cells. CD68+ cells of the control mice did not exhibit any DiD signal.

By the aforementioned result, it can be seen that RBC-EM is mainly distributed in the liver and is endogenous to Kupffer cells (macrophages).

Example 5. Preparation of Exosome Mimetics Derived From Red Blood Cells Loaded With Drug Retroorbital blood samples were collected from Sprague Dawley rats (150 g; 6 weeks old; Hana Corp., Korea). Serum were separated by performing centrifugation at 4° C. and 200 g for 15 min to 20 min, and a mixture (PBS:ACD=9:1 volume ratio) of PBS and acid citrate dextrose (ACD) as an anticoagulant was mixed with blood at a ratio of 4:1.

The mixture was extruded through a 1-μm pore size polycarbonate membrane filter (Nuclepore, Whatman, Inc., Clifton, N.J., USA) using a mini-extruder (Vanti Polar Lipids, Birmingham, Ala., USA). The extruded sample was diluted by adding 20×PBS to the sample, and centrifuged at 4,000 g for 10 min in order to remove RBC, larger vesicles, and debris. The centrifuged sample was filtered by a 0.22 μm syringe filter, and ultra-centrifuged at 4° C. and 100,000 g for 1 hour. After the ultracentrifugation, an obtained pellet was subjected to two-step density gradient ultracentrifugation at 4° C. using iodixanol (OptiPrep™ Density Gradient Medium, Sigma-Aldrich, USA). The exosome mimetics derived from red blood cells (RBC-EM) were obtained at the intersection point of a 60% iodixanol layer and a 20% iodixanol layer, and proteins of RBC-EM were quantified by a BCA analysis method.

A drug at a concentration of 10 to 20 uM/ml was mixed with RBC-EM, and the resulting mixture was incubated at room temperature for 2 hours. As the drug, dexamethasone and curcumin were used. Thereafter, pellets obtained by performing ultracentrifugation at 100,000 g for 1 hour were washed with PBS, and a two-step density gradient ultracentrifugation was performed at 4° C. using iodixanol. A loading efficiency of the drug was calculated using UV spectrometry. The loading efficiency of the drug was about 2%.

Figure 13:
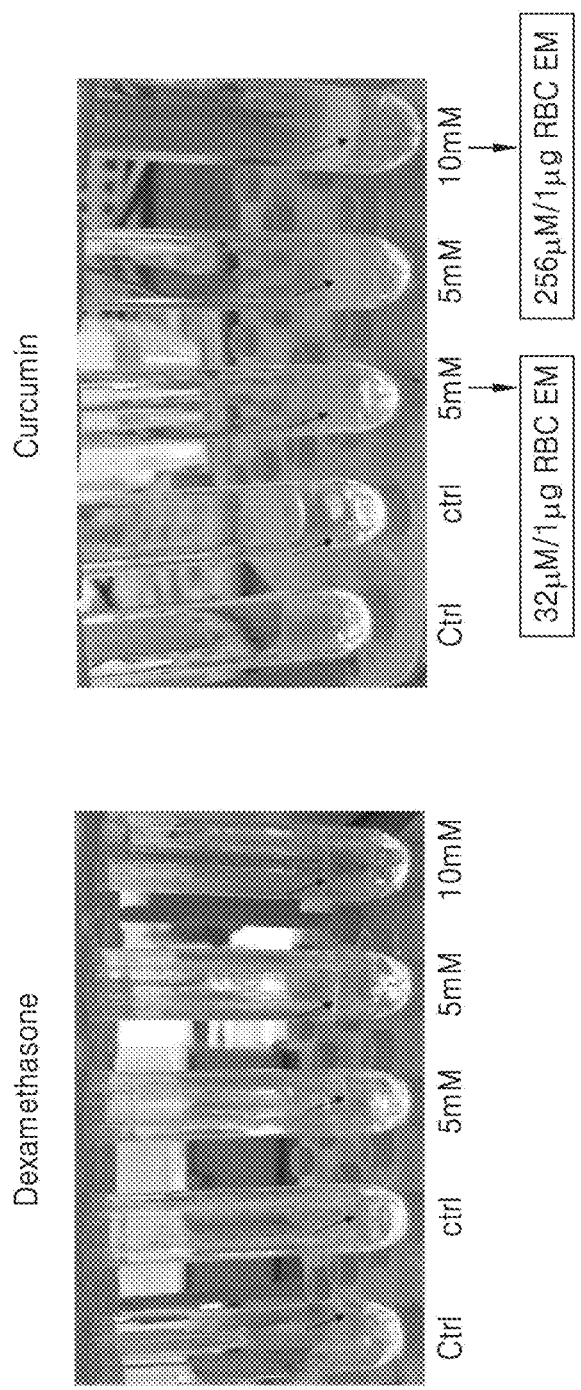
FIG. 13 illustrates the results in which exosome mimetics derived from red blood cells (RBC-EM) are successfully loaded with dexamethasone and curcumin.

FIG. 13 illustrates a result in which RBC-EM is successfully loaded with dexamethasone or curcumin. As illustrated in FIG. 13, it can be observed by the unaided eye that as the concentration of drug added is increased, the number of RBC-EMs loaded with the drug is increased. Based on the result, it can be seen that exosome mimetics derived from red blood cells may be successfully loaded with a drug.

Example 6. Cell Labeling Using $^{99m}$Tc-RBC-EM 6-1. Labeling of Tumor Cells With $^{99m}$Tc Using $^{99m}$Tc-RBC-EM A human atypical thyroid carcinoma 8505C cell line (Deutsche Sammlung von Mikroorganismen und Zellkulturen (DSMZ)) was cultured under a humidified atmosphere of 5% $CO_2$ at 37° C. in Dulbecco's Modified Eagle Medium (DMEM, Invitrogen, Grand Island, N.Y., USA) supplemented with 10% fetal bovine serum (FBS), 10 U/ml penicillin, and 10 μg/ml streptomycin (Invitrogen). The 8505C cells were cultured together with $^{99m}$Tc-RBC-EM with various doses (0, 1, 2, and 4 μCi). 24 hours later, free $^{99m}$Tc-RBC-EM, which had not been absorbed in cells, were washed using PBS. Thereafter, the 8505C cells were cultured in a 20% FBS solution in a 37° C. $CO_2$ incubator for 1, 6, 12, and 18 hours. The uptake values were measured by a gamma-counter (Cobra II, 1 Hewlett Packard, USA) at all the time points, and the amount of radiation measured was shown as a count per minute (cpm) unit. In order to compare the aforementioned results with the results of $^{99m}$Tc-RBC-EM (4 μCi), it was measured whether tumor cells were labeled with $^{99m}$Tc-RBC-EM using free $^{99m}$Tc (4 μCi).

Figure 14A:
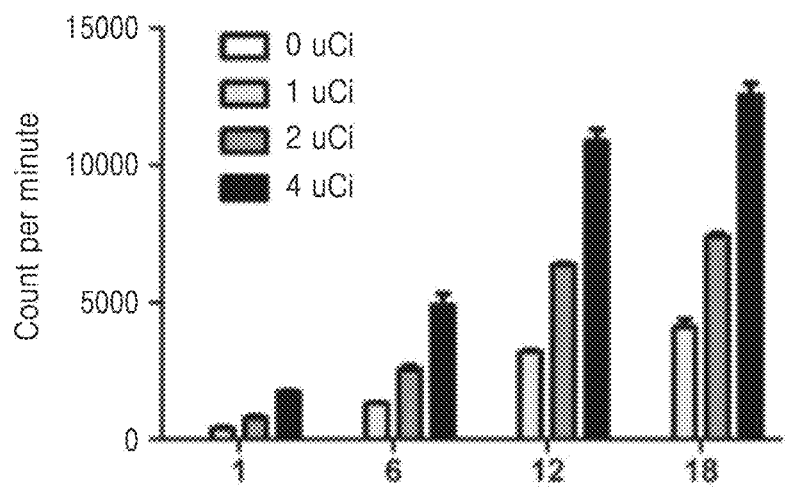
FIG. 14A illustrates amounts of radiation measured in 8505C cells according to the culture time and the dose of $^{99m}$Tc-RBC-EM.
Figure 14B:
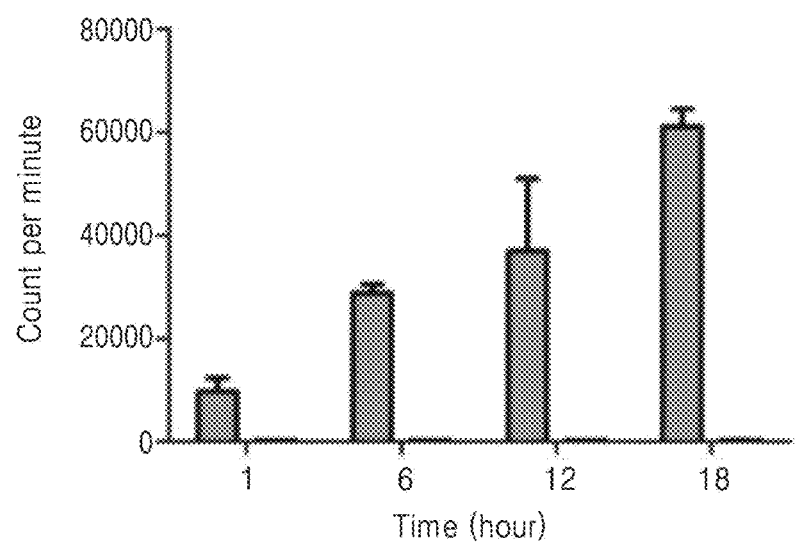
FIG. 14B illustrates amounts of $^{99m}$Tc-RBC-EM and free $^{99m}$Tc with the same dose (4 μCi) absorbed in cells.

FIG. 14A illustrates amounts of radiation of 8505C cells according to the culture time and the dose of $^{99m}$Tc-RBC-EM. As the result illustrated in FIG. 14A, the amounts of radiation were gradually increased according to the dose of $^{99m}$Tc-RBC-EM and the time. Free $^{99m}$Tc absorbed in cells was analyzed as a control. FIG. 14B illustrates amounts of $^{99m}$Tc-RBC-EM and free $^{99m}$Tc with the same dose (4 μCi) absorbed in cells. As illustrated in FIG. 14B, cells rarely absorbed free $^{99m}$Tc, and as the time is increased, the absorption of free $^{99m}$Tc was not increased.

This result shows that $^{99m}$Tc-RBC-EM has an ability to deliver $^{99m}$Tc to cells, and thus cells may be labeled with a radioactive material using $^{99m}$Tc-RBC-EM.

6-2. Labeling of White Blood Cells (WBCs) With $^{99m}$Tc Using $^{99m}$Tc-RBC-EM White blood cells (WBCs) were separated from a buffy coat of a blood sample collected in the same manner as in Example 1-1. The separated sample was centrifuged at 250 g for 10 min. Thereafter, in order to remove the contamination of RBCs, a cell pellet was re-suspended in 3 ml of a lysis buffer (0.83% (w/v) $NH_4Cl$, 10 mM HEPES-NaOH, pH 7.0), and incubated at 37° C. for 7 min. Thereafter, the WBCs were obtained by performing a centrifugation at 250 g at room temperature for 10 min, and used in a subsequent experiment.

In order to label WBCs with $^{99m}$Tc using $^{99m}$Tc-RBC-EM, the separated WBCs were cultured along with $^{99m}$Tc-RBC-EM in a 37° C. and $CO_2$ incubator for 6 hours. In consideration of the short half-life of WBC, WBCs were labeled with $^{99m}$Tc by the same method for a culture time of 6 hours.

After the culture, free $^{99m}$Tc-RBC-EM was removed by performing a centrifugation at 250 g for 10 min, and white blood cells labeled with a radioactive material were constructed by dissolving the collected pellet in PBS, and were named as $^{99m}$Tc-WBC. $^{99m}$Tc-WBC in which white blood cells were labeled with $^{99m}$Tc using $^{99m}$Tc-RBC-EM was additionally used in an in vivo acute inflammation tracking experiment.

Example 7. Tracking of Tumor Using Acute Inflammation Animal Model 7-1. Establishment and Confirmation of Acute Inflammation Mouse Model 6-Week-old female BALB/c nude mice were purchased from Hamamatsu (Shizuoka, Japan). In order to establish an acute inflammation mouse model, 100 μl of 1% carrageenan was injected subcutaneously into the left foot of the BALB/c nude mouse (n=15). 6 hours after the injection, characteristics of acute inflammation in which the left foot was swollen and turned red were observed.

In order to confirm the establishment of acute inflammation, the $^{18}$F-FDG PET/CT imaging was performed. During the injection and imaging, $^{18}$F-FDG 11.1 MBq (300 μCi) was injected intravenously into mice under general anesthesia with 1% to 2% isoflurane in 100% $O_2$, and then $^{18}$F-FDG PET/CT was performed. The images were reconstructed with a 2-dimensional ordered-subsets expectation maximization algorithm (OSEM). No correction for attenuation or scattering was performed.

Figure 15:
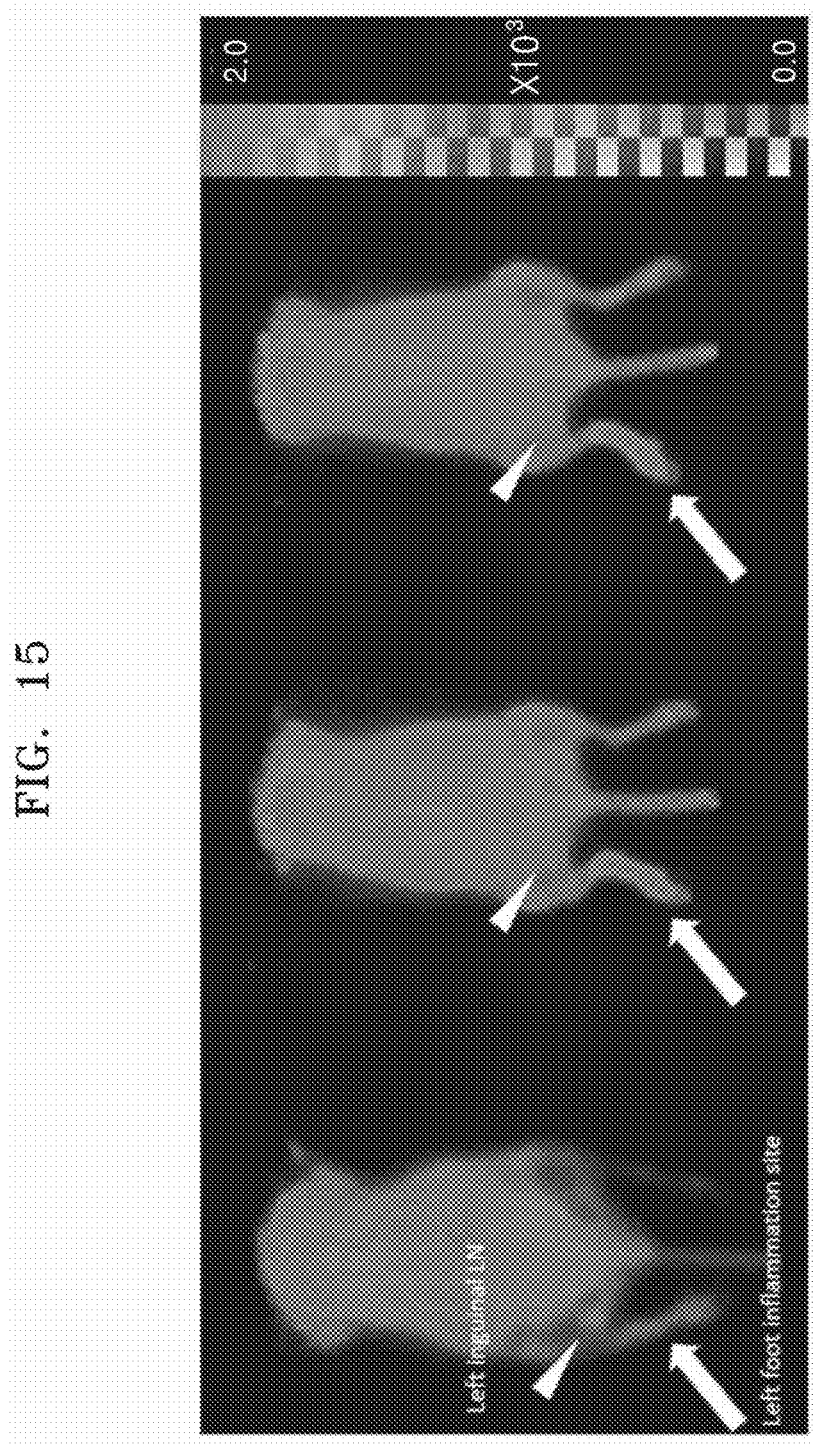
FIG. 15 illustrates a $^{18}$F-FDG PET/CT image of acute inflammatory mice.

FIG. 15 illustrates a $^{18}$F-FDG PET/CT image of acute inflammatory mice. As illustrated in FIG. 15, it was confirmed that acute inflammation had been established in mice by confirming that the glucose metabolism on the left foot was strongly increased and the glucose metabolism was increased in the lymph node of the groin part.

7-2. In Vivo Gamma Camera Imaging

200 µl of 3.7 MBq $^{99m}$Tc-WBC was infused into the tail vein of the acute inflammation mouse model constructed in Example 7-1. Gamma camera images were obtained using a 2 mm pinhole collimator (Infinia II, GE Healthcare, Milwaukee, Wis., USA) for 10 min. During the imaging, mice were continuously anesthetized using 2.5% isoflurane. Gamma camera images were obtained by taking pictures 5 min, 3 hours, 6 hours, 12 hours, and 24 hours after administration of $^{99m}$Tc-WBC.

7-3. Analysis of Biodistribution of $^{99m}$Tc-WBC in Acute Inflammation Mouse Model Mice were sacrificed immediately after the gamma camera imaging of Example 7-2. The uptake amounts of $^{99m}$Tc-WBC in the organ such as the brain, thyroid gland, lungs, heart, liver, spleen, stomach, intestines, bilateral kidneys, bones, muscle, left foot, and right foot were measured by a gamma counter (Cobra II, 1 Hewlett Packard, USA). The resulting values were expressed as a percentage of the amount injected per gram of tissue (% ID/g).

7-4. Tracking of Inflammation Using $^{99m}$Tc-WBC

Figure 16B:
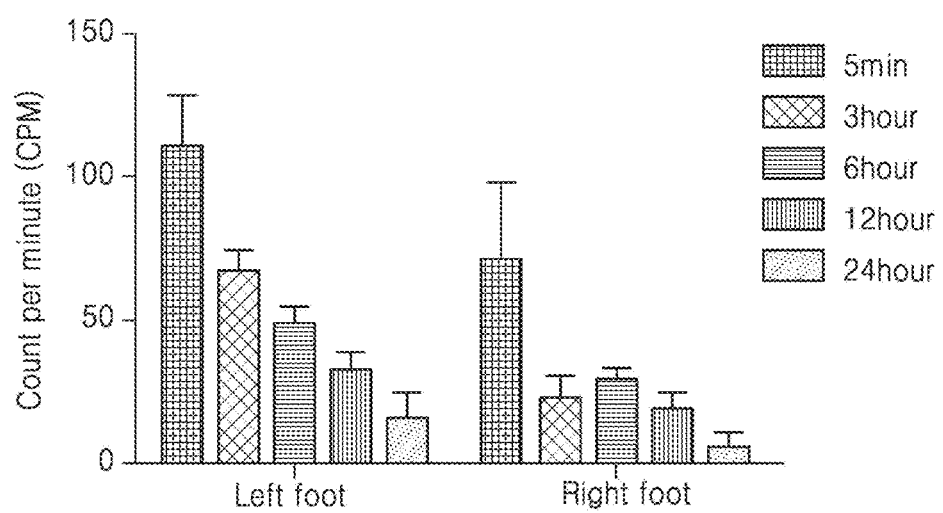
Figure 16C:
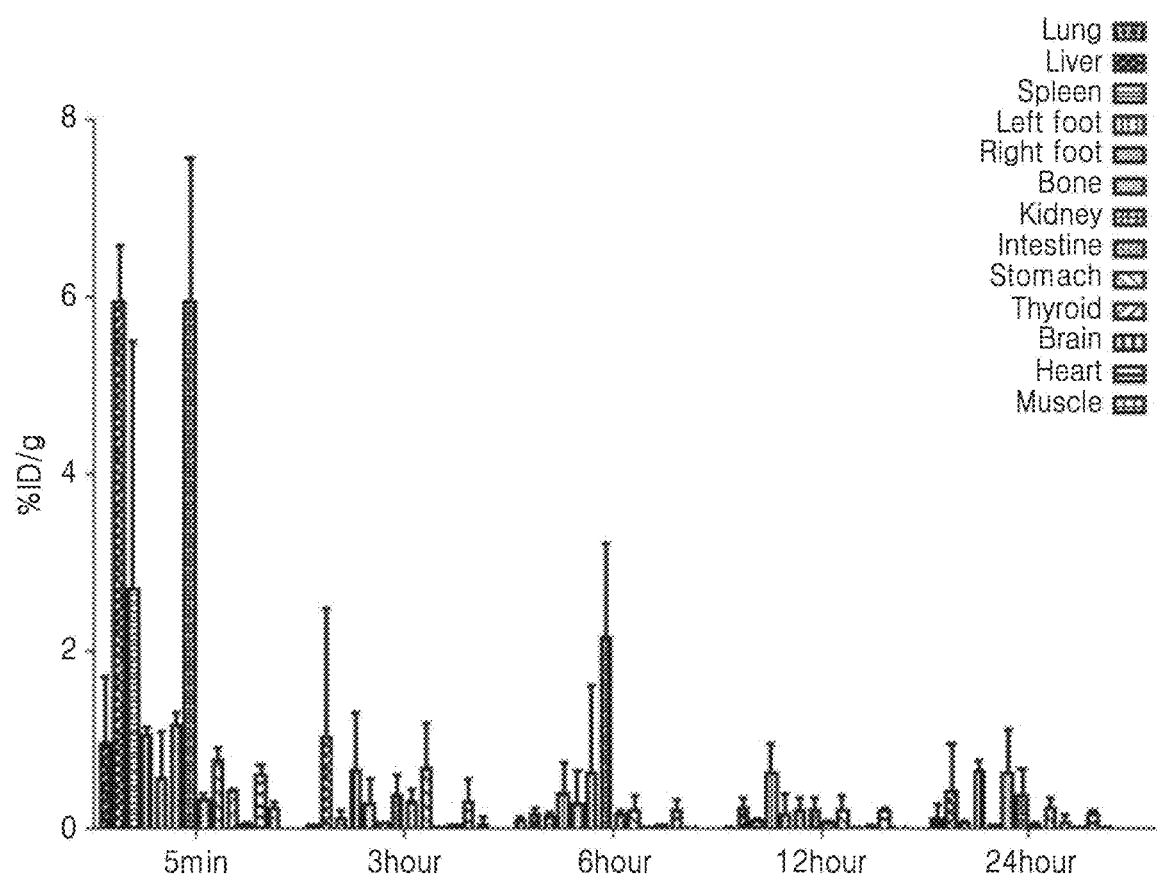
Figure 16D:
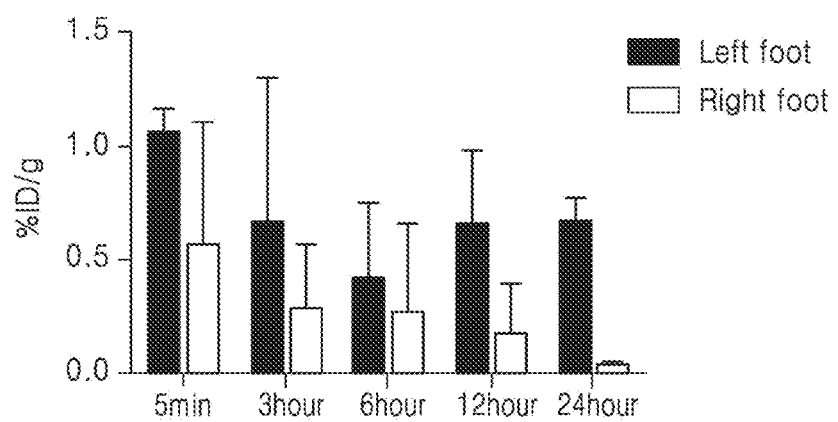

FIGS. 16A to 16D illustrate that in an acute inflammation mouse model, red blood cells labeled with $^{99m}$Tc may be effectively used to track inflammation. Specifically, FIG. 16A illustrates a gamma camera image in an acute inflammation mouse model into which $^{99m}$Tc-WBC is infused via the tail vein. FIG. 16B illustrates amounts of radiation measured from the left and right feet of the acute inflammation mouse model to which $^{99m}$Tc-WBC is injected. FIG. 16C illustrates the biodistribution of $^{99m}$Tc-WBC. FIG. 16D illustrates the amounts of $^{99m}$Tc-WBC uptaken by the left and right legs.

As illustrated in FIG. 16A, the image obtained within 5 min after injection of $^{99m}$Tc-WBC shows that $^{99m}$Tc-WBC is strongly taken up in the liver, spleen, and bladder. As in the result illustrated in FIG. 16B, $^{99m}$Tc-WBC was significantly accumulated in the left leg 3 hours after the injection, and the cpm values were statistically higher in the left foot than those in the right foot. It could be seen that cpm 24 hours after injection was also higher in the left foot than that in the right foot. As illustrated in FIG. 16C, in an ex vivo study, the activities of the liver and the kidneys were significantly higher in the right foot than those in the left foot, the activities of the brain, heart, intestines, muscle, and thyroid gland were significantly lower in the right foot than those in the left foot, but the activities of the liver and kidneys were rapidly decreased 3 hours after the injection. As illustrated in FIG. 16D, the uptake amount of $^{99m}$Tc-WBC in the left foot was higher than that in the right foot at all the time points. 24 hours after the injection, the amount of radiation in the left foot was highest of those of the other organs, and was about 20 times higher than that in the right foot.

The result as described above shows that WBCs may be successfully labeled with $^{99m}$Tc using RBC-EM, and the position of inflammation may be successfully visualized in an animal with an acute inflammation using WBCs labeled with $^{99m}$Tc.

Example 8. Analysis of Position of Exosomes Derived From Red Blood Cells in Rheumatoid Arthritis Animal Model 8-1. Construction of Exosome Mimetics Derived From Red Blood Cells Labeled With Radioactive Material ($^{99m}$Tc) and Fluorescent Material (DiD)

After the RBC-EM obtained in Example 1-1 and 1,1'-dioctadecyl-3,3,3',3'-tetramethylindodicarbocyanine perchlorate (DiD; Thermo Fisher Scientific) were cultured together at room temperature for 20 min, the cultured product was washed with PBS, and DiD-RBC-EM was separated by performing a two-step Opti-Prep density gradient ultracentrifugation in the same manner as in Example 1-1.

Since only $^{99m}$Tc reduced to a low oxidation state is firmly bound to hemoglobin, particularly, the beta-chain of hemoglobin, DiD-RBC-EM was incubated along with tin (II) chloride in order to reduce $^{99m}$Tc. Exosome mimetics derived from red blood cells loaded with the radioactive material ($^{99m}$Tc) and the fluorescent material (DiD) were constructed by incubating DiD-RBC-EM and the same amount of 0.01% tin (II) chloride (Sigma, USA) in a shaker at 37° C. for 5 min, adding technetium-99m ($^{99m}$Tc) to DiD-RBC-EM (DiD-RBC-EM (100 µg):$^{99m}$Tc (111 MBq)) and incubating the resulting mixture in a shaker at 37° C. for 20 min, and the exosome mimetics were named as $^{99m}$Tc-DiD-RBC-EM. When a radioactive purity was less than 95%, an ultracentrifugation was performed at 4° C. and 100,000 g for 1 hour in order to purify $^{99m}$Tc-DiD-RBC-EM.

8-2. Construction of Arthritis Animal Model

A murine collagen-induced arthritis model was performed as previously reported (Journal of Controlled Release 252 (2017): 62-72; PloS one 12.4 (2017)). Bovine type-II collagen (CII; Chondrex, Redmond, Wash., USA) was dissolved at a concentration of 2 mg/ml in 10 mM acetic acid. For primary inoculation (immunization), CII (100 µg) emulsified with the same amount of a complete Freund's adjuvant was injected intradermally into the tail base of 6- to 8-week-old DBA/1J male mice (Japan SLC, Inc., Hamamatsu, Japan). An additional inoculation (booster injection) was performed on day 21 after the primary inoculation of CII (100 µs) in the complete Freund's adjuvant. Clinical characteristics of arthritis of mice were observed daily from day 22. Two independent observers observed clinical characteristics of arthritis three times per week from day 22 after the primary inoculation. The clinical severity of arthritis was recorded according to a grade from 0 to 4 as previously reported (Arthritis & Rheumatism 65.7 (2013)). When arthritis occurred, mice were randomly selected and used in a subsequent experiment.

8-3. Gamma Camera Imaging and Fluorescent Imaging

The gamma camera images were captured and taken for 10 min using a 2 mm pinhole collimator (Infinia II, GE Healthcare, Milwaukee, Wis., USA). 200 µl of ~MBq $^{99m}$Tc-DiD-RBC-EM was infused into the tail vein of mice. As a control, the same amount of free $^{99m}$Tc was infused. During the imaging, mice were continuously anesthetized using 2.5% isoflurane. The gamma camera images were taken 1, 3, 12, or 24 hours after $^{99m}$Tc-DiD-RBC-EM and free 99mTc were infused.

C57BL/6 mice were anesthetized with isoflurane, and $^{99m}$Tc-DiD-RBC-EM or PBS was infused into the tail vein via intravenous injection. 1, 3, 12, or 24 hours after the infusion, fluorescent imaging was performed using an in vivo imaging system (IVIS Lumina III instrument, PerkinElmer) [wavelengths: Excitation—644 nm and emission—665 nm; imaging parameters: binning—4, smoothing—3×3, Field of subject (stage—D): 12.5 cm, height of subject image: 1.5 cm].

8-4. Analysis of Position of $^{99m}$Tc-DiD-RBC-EM

Figure 17A:
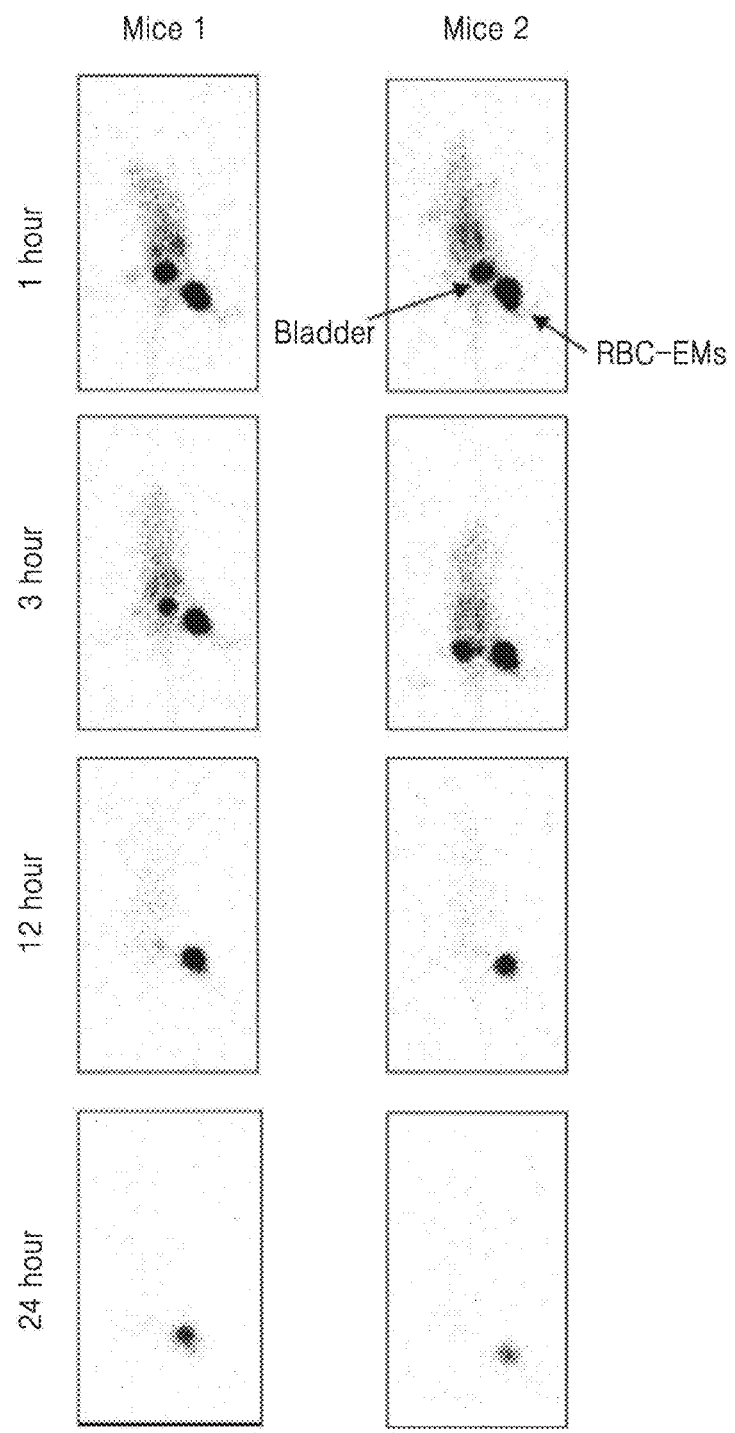
FIGS. 17A and 17B illustrate the results of performing gamma camera imaging after infusing $^{99m}$Tc-DiD-RBC-EM into the articular cavity of an animal model with rheumatoid arthritis. Specifically.
Figure 17B:
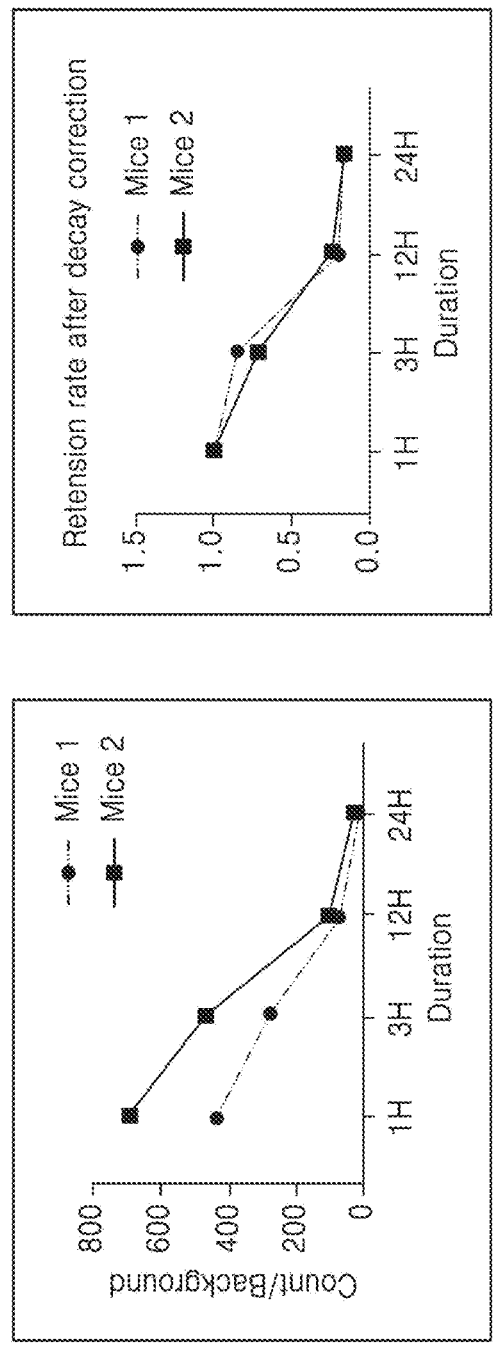

FIGS. 17A and 17B illustrate the results of performing gamma camera imaging after $^{99m}$Tc-DiD-RBC-EM is infused into the articular cavity of an animal model with rheumatoid arthritis. Specifically, FIG. 17A illustrates a gamma camera image of mice with rheumatoid arthritis, and FIG. 17B quantitatively illustrates amounts of measured radiation. The left graph of FIG. 17B illustrates absolute values of amounts of radiation measured (background corrected counts) in a portion injected into the arthritic lesion, and the right graph illustrates the amounts of radiation (retention rate) remaining in the injected lesion after radiation decay correction in the same data. That is, FIG. 17 illustrates how much radiation remains in the injected lesion when the radiation dose on hour 1 is seen as 100% (corresponding to 1.0 in the graph).

As illustrated in FIGS. 17A and 17B, it could be confirmed that $^{99m}$Tc-DiD-RBC-EM remained in the articular cavity without significantly moving to other organs up to 24 hours after the infusion.

Figure 18A:
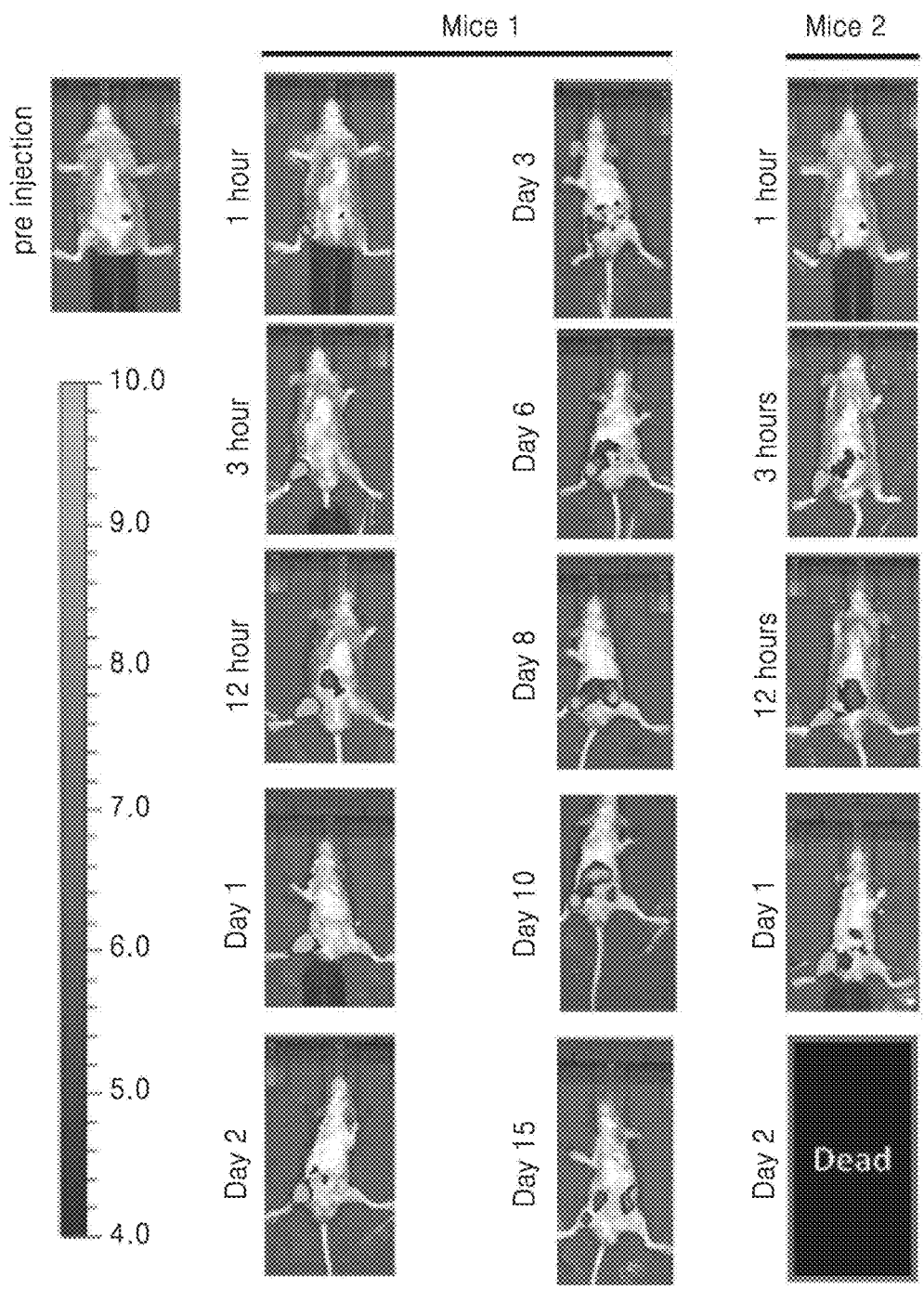
FIG. 18A illustrates a fluorescent image over time, and FIG. 18B quantitatively illustrates amounts of fluorescent material measured.
Figure 18B:
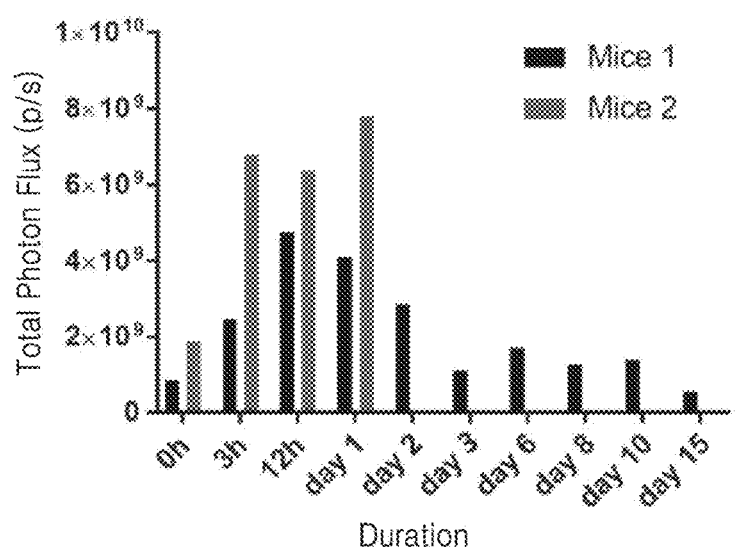

As a result of performing fluorescent imaging after $^{99m}$Tc-DiD-RBC-EM is infused into the articular cavity of the animal model with rheumatoid arthritis, FIG. 18A illustrates a fluorescent image over time, and FIG. 18B quantitatively illustrates amounts of fluorescent material measured. The No. 2 mouse died on day 2, but it can be seen that $^{99m}$Tc-DiD-RBC-EM remains in the articular cavity up to day 15 in the IVIS images of the No. 1 mouse. It is determined as autofluorescence that fluorescence is observed in addition to the articular cavity on 12th hour, day 3, day 6, day 8, day 10, and day 15 in the IVIS images of the No. 1 mouse. As illustrated in FIG. 18, $^{99m}$Tc-DiD-RBC-EM are remaining in the articular cavity without significantly moving to other organs in the same manner as in the gamma camera imaging result.

Example 9. Analysis of Position of Exosomes Derived From Red Blood Cells in Tumor Animal Model 9-1. Construction of Tumor Animal Model Nude mice transplanted subcutaneously with Ca162/effluc ($5 \times 10^6$ cells) in the lower right region were grown for 6 weeks. After the mice were anesthetized with 2.5% isofluorane and 100 µl of D-luciferin (3 mg/mouse; Caliper) was injected intraperitoneally for bioluminescence images, a bioluminescence imaging (hereinafter, referred to as BLI) was performed using the IVIS Lumina III imaging system. Subsequently, BLI was observed up to 6 weeks, and the mice were used in an additional experiment.

9-2. Construction of Exosome Mimetics Derived From Red Blood Cells Labeled With Fluorescent Material (Porphyrin)

Red blood cells were obtained by the method described in Example 1-1, diluted by adding PBS to red blood cells (RBC:PBS=1:9 by volume ratio), and porphyrin was added thereto so as to have a concentration of 0.1%. The mixture was extruded once to four times through a 1-µm pore size polycarbonate membrane filter (Nuclepore, Whatman, Inc., Clifton, N.J., USA) using a mini-extruder (Vanti Polar Lipids, Birmingham, Ala., USA).

The labeled exosome mimetics derived from red blood cells labeled with porphyrin were obtained at the intersection point of a 60% iodixanol layer and a 20% iodixanol layer, and were immediately used without an additional treatment. The obtained exosome mimetics derived from red blood cells labeled with porphyrin were named as porphyrin-RBC-exosome mimetics (porphyrin-RBC-EM).

9-3. Fluorescent Imaging

C57BL/6 mice were anesthetized with isofluorane, and porphyrin-RBC-EM or free porphyrin was infused into the tumor of the tumor animal model and into the hypodermis on the tendon side. 1 to 288 hours after the infusion, fluorescent imaging was performed using an in vivo imaging system (IVIS Lumina III instrument, PerkinElmer) [wavelengths: Excitation—644 nm and emission—665 nm; imaging parameters: binning—4, smoothing—3×3, Field of subject (stage—D): 12.5 cm, height of subject image: 1.5 cm]. Ex vivo fluorescent imaging was performed by collecting the subcutaneous tissue, liver, spleen, heart, lungs, kidneys, and tumors after the imaging, and a quantitative analysis was performed using IVIS software (Living Image Software, PerkinElmer).

9-4. Position of Porphyrin-RBC-EM

Figure 19:
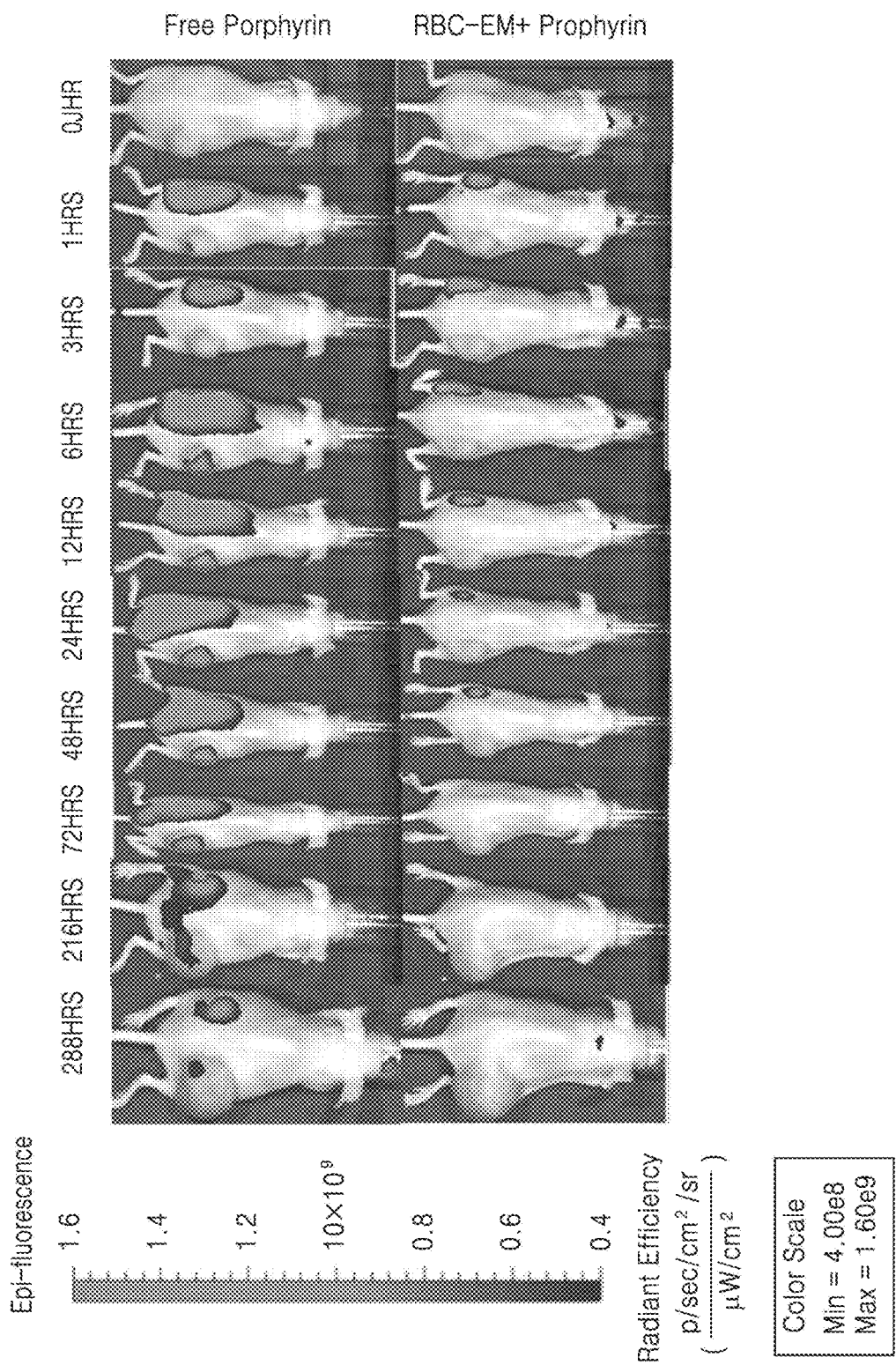
FIG. 19 illustrates a fluorescent image over time when RBC-EM-porphyrin is infused into the tumor.
Figure 20A:
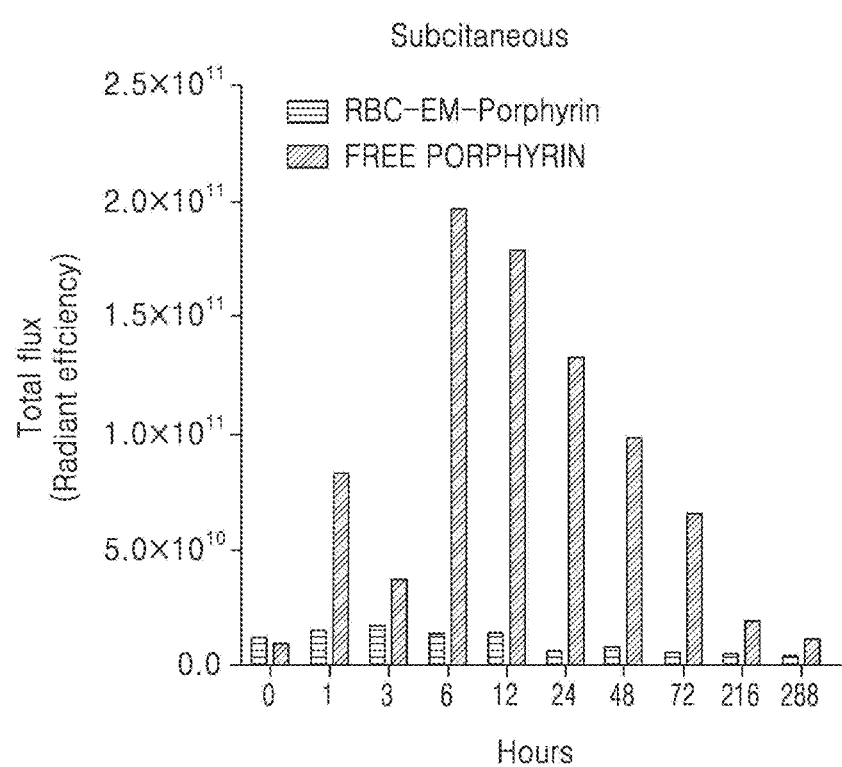
FIG. 20A illustrates amounts of porphyrin measured subcutaneously when RBC-EM-porphyrin is infused subcutaneously.
Figure 20B:
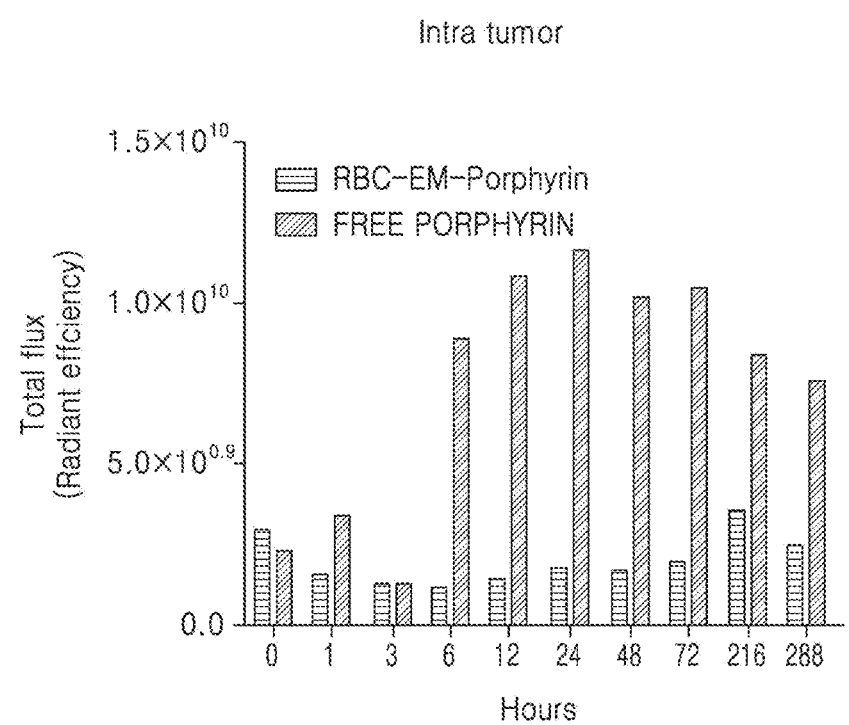
FIG. 20B illustrates amounts of porphyrin measured in tumor when RBC-EM-porphyrin is infused into the tumor.

RBC-EM was loaded with porphyrin, and then injected into the hypodermis and tumors. FIG. 19 illustrates a fluorescent imaging over time when RBC-EM-porphyrin is infused into the tumor. The HRS described in FIG. 19 means time. FIG. 20 illustrates amounts of porphyrin measured subcutaneously and in the tumor when RBC-EM-porphyrin is infused subcutaneously and into the tumor. As illustrated in FIGS. 19 and 20, it can be confirmed in an in vivo IVIS imaging that RBC-EM-porphyrin remains in the tumor up to day 12.

Figure 21A:
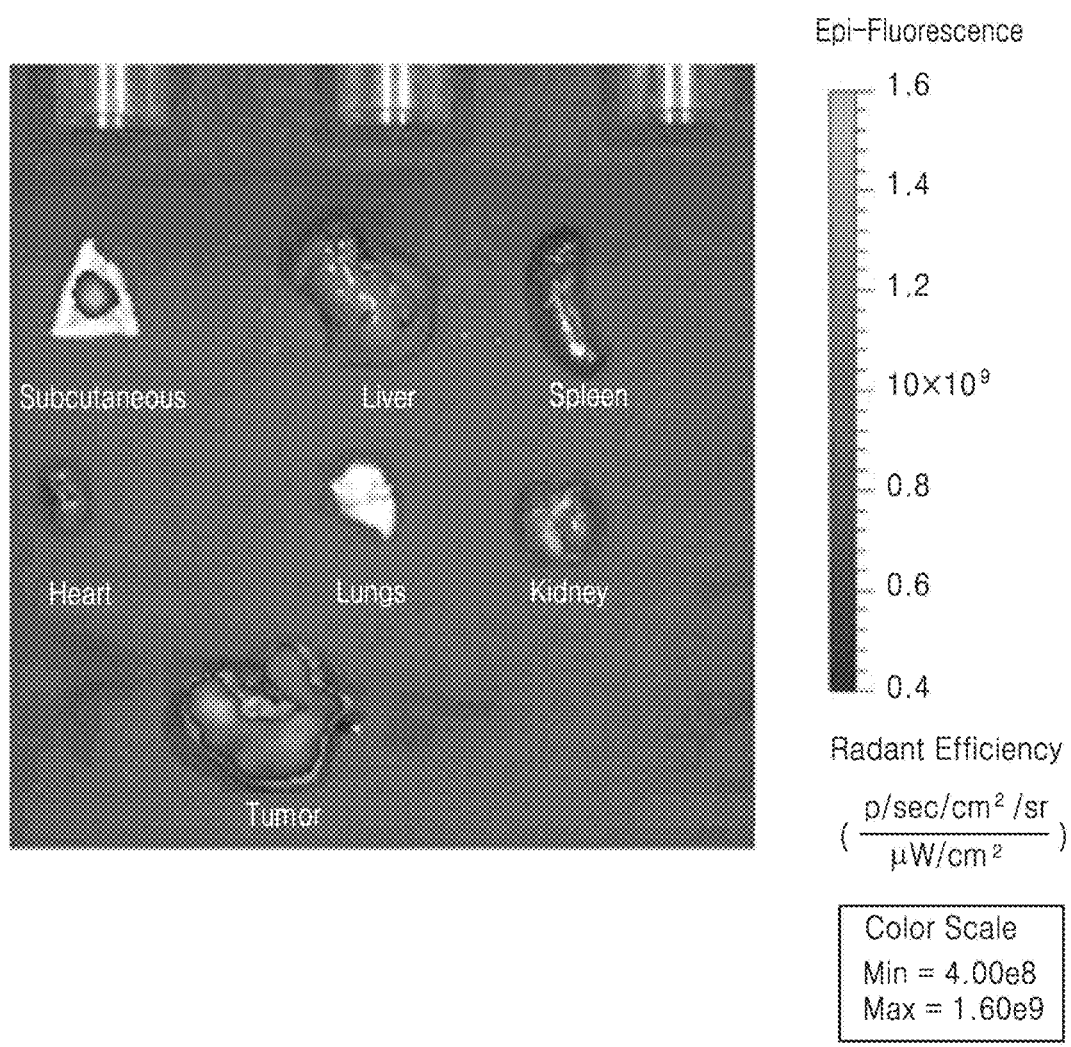
FIG. 21A illustrates an ex-vivo fluorescent image of various organs and FIG. 21B illustrates quantitative values of porphyrin measured in various organs.
Figure 21B:
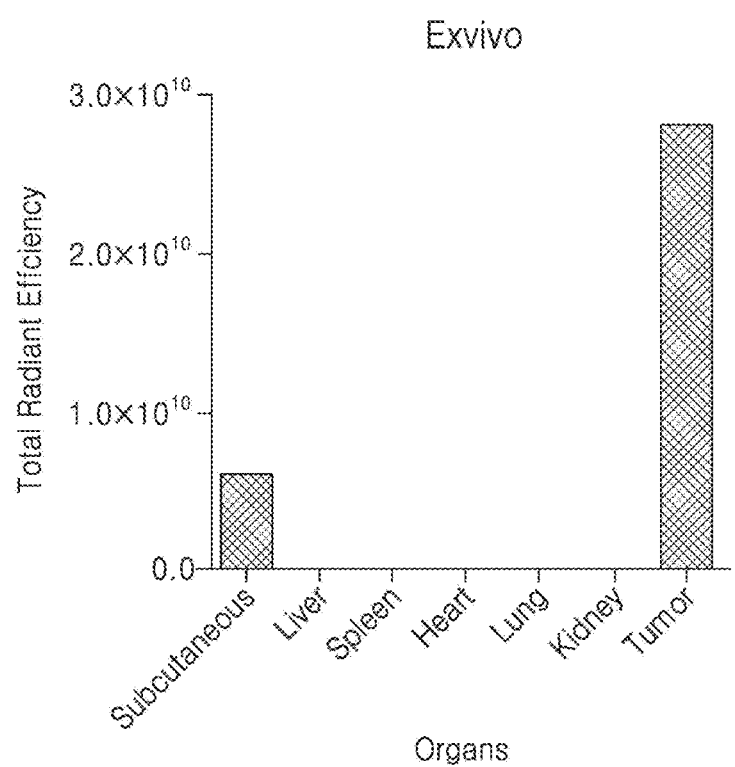

On 12 days, fluorescent imaging was performed by sacrificing mice and collecting subcutaneous tissues, liver, spleen, heart, lungs, kidneys, and tumor tissues. FIG. 21 illustrates an ex-vivo fluorescent image of various organs and the amount of porphyrin quantitatively measured. As illustrated in FIG. 21, it can be seen that RBC-EM-porphyrin remains in the tumor without significantly moving to other organs in the same manner as in the results because the amount of porphyrin in the hypodermis and tumor is remarkably high.

Statistical Analysis

The experimental result values are shown as mean±standard deviation (SD). The statistical significance is determined (student t-test) by GraphPad Prism5 software version 7.04 (GraphPad Software, Inc., La Jolla, Calif., USA). P values less than 0.05 were considered statistically significant.

What is claimed is:

1. A composition for material delivery, comprising exosome mimetics derived from red blood cells loaded with a target material, wherein the exosome mimetics are vesicles artificially prepared by extruding red blood cells by a filter, wherein the target material comprises technetium-99m ($^{99m}$Tc), wherein the exosome mimetics comprises hemoglobin derived from red blood cells and the technetium-99m ($^{99m}$Tc) is bound to hemoglobin inside the exosome mimetics derived from red blood cells, wherein the exosome mimetics derived from red blood cells have a diameter of 100 nm to 300 nm.

2. The composition of claim 1, wherein the target material further comprises one or more selected from the group consisting of a drug, a radioactive material other than technetium-99m, and a fluorescent material.

3. The composition of claim 2, wherein the drug is one or more selected from the group consisting of a compound, a peptide, a protein, and a nucleic acid.

4. The composition of claim 2, wherein the radioactive material is a diagnostic radionuclide or a therapeutic radionuclide.

5. The composition of claim 4, wherein the therapeutic radionuclide is one or more selected from the group consisting of $^{131}$I, $^{186}$Re, $^{188}$Re, $^{153}$Sm, and $^{32}$P.

6. The composition of claim 2, wherein the fluorescent material is one or more selected from the group consisting of a fluorescent protein, a photoprotein, a luciferase, and a fluorescent dye.

7. The composition of claim 1, wherein the composition for material delivery is used to treat a liver disease.

8. The composition of claim 1, wherein the composition for material delivery is used to treat arthritis.

9. The composition of claim 1, wherein the composition for material delivery is used to treat tumors.

10. The composition for claim 1, wherein the composition for material delivery is used to label cells.

11. A method for preparing the composition for material delivery of claim 1, the method comprising:
 (a) obtaining exosome mimetics derived from red blood cells, wherein the exosome mimetics are vesicles artificially prepared by extruding red blood cells by a filter;
 (b) incubating a mixture in which the exosome mimetics derived from red blood cells obtained in step (a) and a target material are mixed;
 (c) obtaining a pellet by ultracentrifuging the mixture incubated in step (b);
 (d) separating exosome mimetics derived from red blood cells loaded with a target material by washing the pellet obtained in step (c) and using a density gradient;
 (e) incubating a mixture in which the exosome mimetics derived from red blood cells separated in step (d) and tin (II) chloride are mixed; and
 (f) adding technetium-99m ($^{99m}$Tc) to the mixture incubated in step (e) and incubating the resulting mixture.

12. The method of claim 11, wherein the target material is one or more selected from the group consisting of a drug, a radioactive material other than technetium-99m, and a fluorescent material.

13. A contrast medium comprising the composition for material delivery of claim 1.

14. The contrast medium of claim 13, wherein the contrast medium is applied to nuclear medical imaging.

15. The contrast medium of claim 14, wherein the nuclear medical imaging is positron emission tomography (PET) or single-photon emission computed tomography (SPECT), or gamma camera imaging.

* * * * *

UNITED STATES PATENT AND TRADEMARK OFFICE
CERTIFICATE OF CORRECTION

| | | |
|---|---|---|
| PATENT NO. | : 11,446,402 B2 | Page 1 of 1 |
| APPLICATION NO. | : 16/670044 | |
| DATED | : September 20, 2022 | |
| INVENTOR(S) | : Ahn et al. | |

It is certified that error appears in the above-identified patent and that said Letters Patent is hereby corrected as shown below:

On the Title Page (*) Notice: delete the following "This patent is subject to a terminal disclaimer"

Signed and Sealed this
Twenty-eighth Day of February, 2023

Katherine Kelly Vidal
*Director of the United States Patent and Trademark Office*